US009400274B2

(12) United States Patent
Swinnen et al.

(10) Patent No.: US 9,400,274 B2
(45) Date of Patent: Jul. 26, 2016

(54) CANCER PHOSPHOLIPIDOME

(71) Applicant: Katholieke Universiteit Leuven, Leuven (BE)

(72) Inventors: Johannes Victor Maria Swinnen, Leuven (BE); Jelle Machiels, Leuven (BE); Eyra Marie-Jeanne Edel Leopold Marien, Leuven (BE); Muralidhara Rao Bagadi, Leuven (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 181 days.

(21) Appl. No.: 13/849,885

(22) Filed: Mar. 25, 2013

(65) Prior Publication Data
US 2014/0220613 A1    Aug. 7, 2014

Related U.S. Application Data

(63) Continuation-in-part of application No. PCT/EP2011/066568, filed on Sep. 23, 2011.

(30) Foreign Application Priority Data

Sep. 24, 2010  (GB) .................................. 1016139.6
Feb. 10, 2011  (WO) ................. PCT/EP2011/051936

(51) Int. Cl.
*G01N 33/50* (2006.01)
*G01N 33/574* (2006.01)

(52) U.S. Cl.
CPC .......... *G01N 33/5091* (2013.01); *G01N 33/574* (2013.01); *G01N 2333/918* (2013.01)

(58) Field of Classification Search
None
See application file for complete search history.

(56) References Cited

U.S. PATENT DOCUMENTS

2009/0220512 A1*  9/2009  Nakamura et al. ......... 424/139.1

FOREIGN PATENT DOCUMENTS

WO    2011098509 A1    8/2011

OTHER PUBLICATIONS

Philip B. W. Smith, Characterization of Bacterial Phospholipids by Electrospray Ionization Tandem Mass Spectrometry, Anal. Chem. 1995, 67, 1824-1830.*
Kiyoshi Satouchi, Takako Mizuno, Yoshiko Samejima, and Kunihiko Saito, Molecular Species of Phospholipid in Rat Hepatomas and in Fetal, Regenerating, and Adult Rat Livers, 1984, Cancer Research, vol. 44, pp. 1460-1464.*
Koen Brusselmans and Johannes V. Swinnen, The Lipogenic Switch in Cancer. Mitochondria and Cancer, Keshav K. Singh and Leslie C. Costello, Ed., Springer, New York, US, Jan. 1, 2009, pp. 39-59, ISBN: 978-0-387-84834-1.*

(Continued)

*Primary Examiner* — Ralph Gitomer
*Assistant Examiner* — Trent Clarke
(74) *Attorney, Agent, or Firm* — Dinsmore & Shohl LLP

(57) ABSTRACT

In general, the present invention relates to identification of lipidome biomarkers for cancer analysis and it provides prognostic and predictive methods and kits for cancer diagnosis and subtyping and for diagnosing and/or predicting the evolution of a tumor and its response to lipid metabolism-targeted or other types of therapy in a subject, by making use of phospholipid (PL) profiling, wherein changes in the combined acyl chain length of intact body fluid-derived or tumor-derived phospholipid species is indicative of an elongation phenotype.

23 Claims, 17 Drawing Sheets

(56) References Cited

OTHER PUBLICATIONS

Miriam Schwalbe-Herrmann, Jan Willmann, Dieter Leibfritz, Separation of phospholipid classes by hydrophilic interaction chromatography detected by electrospray ionization mass spectrometry, 2010, Journal of Chromatography A, vol. 1217, pp. 5179-5183 (online May 19, 2010).*

Bo Zhang and Keijiro Saku, Control of matrix effects in the analysis of urinary F2-isoprostanes using novel multidimensional solid-phase extraction and LC-MS/MS, 2007, Journal of Lipid Research, vol. 48, pp. 733-744.*

Hideo Ogiso, Takahiro Suzuki, Ryo Taguchi, Development of a reverse-phase liquid chromatography electrospray ionization mass spectrometry method for lipidomics, improving detection of phosphatidic acid and phosphatidylserine, 2008, Analytical Biochemistry, vol. 375, pp. 124-131.*

Beckers et al., "Chemical Inhibition of Acetyl-CoA Carboxylase Induces Growth Arrest and Cytotoxicity Selectively in Cancer cells", Cancer Research vol. 67, No. 17, pp. 8180-8187, Sep. 1, 2007.

Crowe et al., "Fatty acid composition of plasma phospholipds and risk of prostate cancer in a case-control analysis nested within the European Prospective Investigation into Cancer and Nutrition", The American Journal of Clinical Nutrition vol. 88, No. 5, pp. 1353-1363, Nov. 2008.

Jump et al., "Soraphen A, an inhibitor of acetyl CoA carboxylase activity, interferes with fatty acid elongation", Biochemical Pharmacology, vol. 81, No. 5, pp. 649-660, Mar. 1, 2011.

Menendez et al., "Fatty acid synthase and the lipogenic phenotype in cancer pathogenesis", Nature Reviews/Cancer, vol. 7, No. 10, pp. 763-777, Oct. 2007.

Milne et al., "Lipidomics: An analysis of cellular lipids by ESI-MS", Methods: A Companion to Methods in Enzymology, vol. 39, No. 2, pp. 92-103, Jun. 1, 2006.

Olsen et al., "Fatty acid synthesis is a therapeutic target in human liposarcoma", International Journal of Onocology vol. 36, No. 5, pp. 1309-1314, May 5, 2010.

Rysman et al., "De novo Lipogenesis Protects Cancer Cells from Free Radicals and Chemotherapeutics by Promoting Membrane Lipid Saturation", American Association for Cancer Research, vol. 70, No. 20, pp. 8118-8126, Oct. 15, 2010.

Shimma et al., "MALDI-based imaging mass spectrometry revealed abnormal distribution of phospholipids in colon cancer liver metastasis", Journal of Chromatography B: Biomedical Sciences & Applications, vol. 855, No. 1, pp. 98-103, Jul. 20, 2007.

Swinnen et al., "Increased lipogenesis in cancer cells: new players, novel targets", Current Opinion in Clinical Nutrition and Metabolic Care, Rapid Science Publishers, vol. 9, No. 4, pp. 358-365, Jul. 1, 2006.

International Application PCT/EP2011/066568 Search Report dated Dec. 9, 2011.

International Preliminary Report on Patentability for Application PCT/EP2011/066568 dated Nov. 6, 2012.

Certified Copy of GB Application No. 1016139.6 filed Sep. 24, 2010.

* cited by examiner

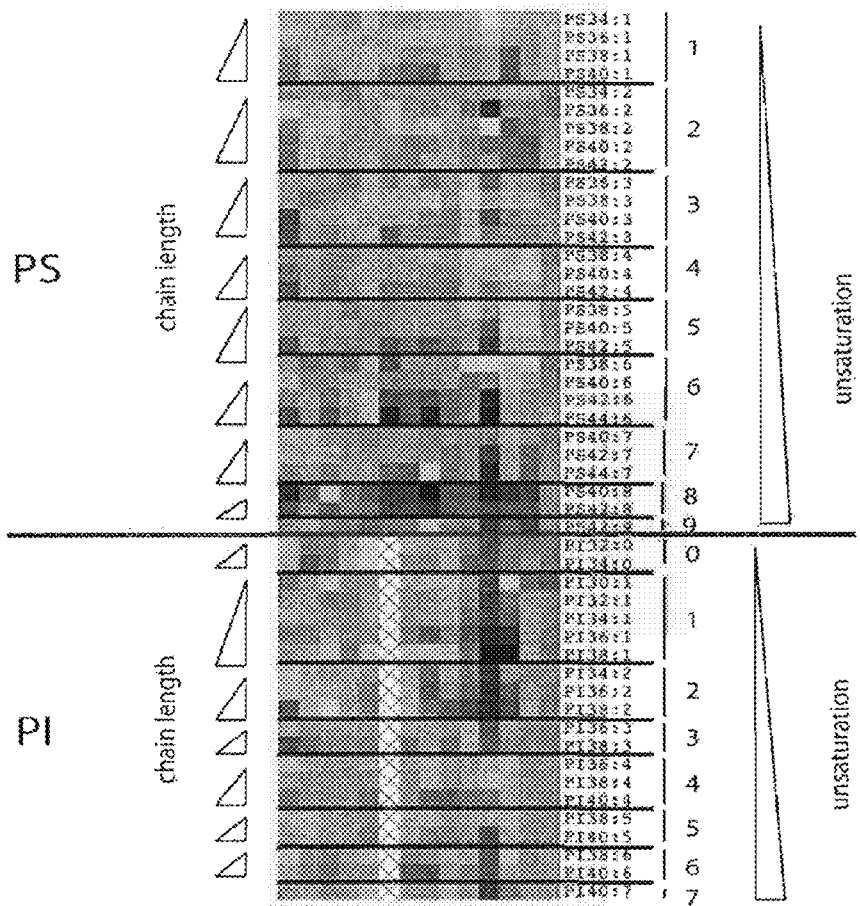

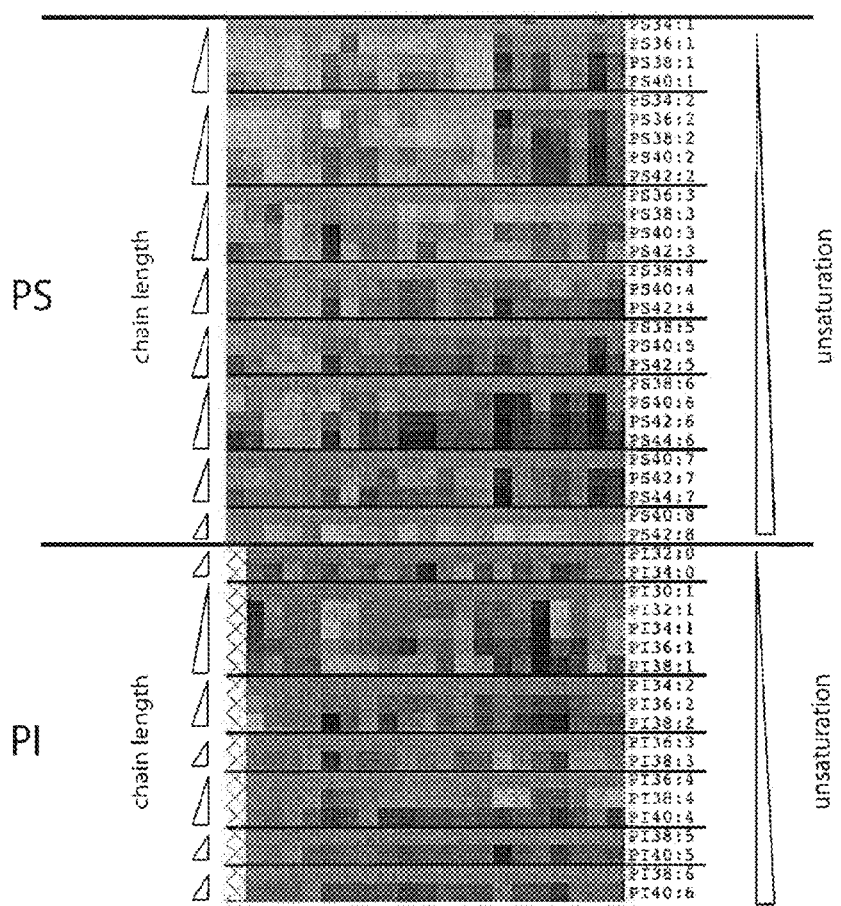

CANCER PHOSPHOLIPIDOME

CROSS-REFERENCE TO RELATED APPLICATIONS

This application is filed under 35 U.S.C. §111(a) as a continuation-in-part of International Patent Application No. PCT/EP2011/066568, which international application designates the United States, and which claims the benefit of International Patent Application No. PCT/EP2011/051936, filed Feb. 10, 2011, and Great Britain Application No. 1016139.6, filed Sep. 24, 2010.

TECHNICAL FIELD

In general, the present invention relates to identification of lipidome biomarkers for cancer analysis and it provides prognostic and predictive methods and kits for cancer diagnosis and subtyping and for predicting the evolution of a tumor and its response to lipid metabolism-targeted or other types of therapy in a subject, by making use of phospholipid (PL) profiling, wherein changes in the acyl chain length of intact body fluid-derived or tumor-derived phospholipid species is indicative of an elongation phenotype. More in particular, wherein changes in the relative expression level of phospholipid species within the same head group class, having the same saturation level but different acyl chain lengths are indicative of a more aggressive elongation phenotype. Said elongation phenotype, separately or combined with the lipogenic phenotype being associated with the presence of cancer, of specific cancer subtypes, of a more aggressive phenotype, or of responsiveness to inhibitors of lipogenic enzymes, elongases, or other types of therapy, including tyrosine kinase-targeted therapy. Moreover the present invention relates generally to phenotyping cancers based on elongation and lipogenic phenotypes for linking this to the biological condition of a biological sample, more particularly a sample of a cancer, for identifying the morbidity, stage or behaviour of the cancer.

BACKGROUND TO THE INVENTION

Cancer is recognized by uncontrolled growth of cells, which form a tumor and ultimately may invade other tissues (metastasis). Cancer affects people of all ages, and is a major cause of human death whereby in particular lung cancer, stomach cancer, colorectal cancer and liver cancer are the deadliest ones. The most commonly occurring cancer in men is prostate cancer and in women it is breast cancer.

Each year 11 million people worldwide are diagnosed with cancer. Almost 7 million die from the disease. Treatment options of many cancer types and the success rate of intervention largely depend on the stage of the disease at the time of diagnosis. In many cases, early detection is of utmost importance as it greatly increases the chances for successful treatment. The implementation of screening programs and tools for early detection and better diagnosis is of great importance. However, this also increases the detection rate of latent and clinically irrelevant tumors. This poses a great risk of overtreatment and is therefore a tremendous clinical dilemma since no effective tests for disease progression are available. On the other hand, a substantial number of patients will develop clinical metastatic disease or already presents with occult metastases at the time of staging. Moreover, tumors often respond differently to a given type of therapy and often acquire resistance to therapy. These situations emphasize the need for reliable criteria and tools for treatment decision and follow-up in order to implement a more personalized and adequate treatment.

Currently, cancer diagnosis, cancer subtyping and treatment decision of many cancers is largely based on the histopathological TNM (tumor, node, metastasis) system, the histological differentiation of the primary tumor, and immunohistochemistry. As these systems provide only an ad hoc picture of the tumor based on few parameters, multiparameter molecular-based insights in the tumor characteristics will undoubtedly help to more accurately predict progression and therapy response and will aid in the selection of more appropriate primary and/or adjuvant treatment options. Recent advances in molecular analytical methods hold significant promise in this respect and have the power to revolutionize the ways cancer is diagnosed and treated.

Up to now, most efforts towards multiparameter molecular characterization and staging of cancer are carried out at the level of DNA, RNA or proteins (screening for genomic mutations, high throughput genome or exosome sequencing, analysis of epigenetics, transcriptome analysis, or protein profiling). For example, gene expression profiling can predict clinical outcomes of prostate cancer (G. V. et al., J. CHn. Invest. 113: 913-923 (2004)) as well as breast cancer (Van't Veer et al. Nature 415: 530-536 (2002)).

Nevertheless, changes more downstream are perhaps of more significance as they represent more distal endpoints of cellular regulation, integrating diverse (epi)genetic, regulatory and environmental cues. Of particular interest in this respect are changes in membrane lipid composition.

Functioning as barriers that separate and compartmentalize the cell's content, membranes function as unique interfaces at which numerous cellular processes (including signaling, nutrient transport, cell division, respiration, cell death mechanisms, etc) are concentrated and regulated. An ever increasing body of evidence indicates that membrane lipids, and particularly changes in phospholipid species play a central role in this regulation (Marguet D, Lenne P F, Rigneault H, He H T (2006) Dynamics in the plasma membrane: how to combine fluidity and order. EMBO J 25: 3446-3457).

Phospholipids are a complex class of cellular lipids that are composed of a headgroup (choline, ethanolamine, serine, inositol, etc) and 1 to 4 fatty acyl chains that can differ both in length and in the number of unsaturations (double bonds), leading to hundreds of different species. The building blocks for these lipids can be taken up from the circulation, however, some can also be synthesized de novo. Most cells express elaborate pathways that dynamically modify lipid structures. This can change their chemical properties dramatically and locally modulates the biochemical and biophysical properties of membranes.

There is mounting evidence that in tumors, phospholipid metabolism is dramatically different from normal tissue. Whereas most normal tissues acquire the bulk of the required lipids from the circulation, tumor cells frequently synthesize the majority of their lipids de novo (Brusselmans, K., and Swinnen, J. V. (2009) The lipogenic switch in Cancer. In Mitochondria and Cancer, K K Singh and L. C. Costello, Eds, Springer, New York, USA pp. 39-59). This is illustrated by a dramatic overexpression of lipogenic enzymes such as fatty acid synthase in tumors, particularly in those with a poor prognosis. Activation of this lipogenic pathway involves changes at all levels of enzyme regulation (genetic changes, enhanced transcription and translation, protein stabilization and phosphorylation, allosteric regulation and substrate flux) and occurs downstream of various common oncogenic events (loss of PTEN, activation of Akt, loss of BRCA1, steroid hormone action, tumor-associated hypoxia, etc.) (Swinnen, J. V., Brusselmans, K., and Verhoeven, G. (2006). Increased lipogenesis in cancer cells: new players, novel targets. Curr Opin Clin Nutr Metab Care 9, 358-365).

Conversely, other tumor types or tumor subtypes seem to activate the uptake mechanisms of fatty acids for instance by expressing lipoprotein lipase (Kuemmerle N B, Rysman E, Lombardo P S, Flanagan A J, Lipe B C, Wells W A, Pettus J R, Froehlich H M, Memoli V A, Morganelli P M, Swinnen J V, Timmerman L A, Chaychi L, Fricano C J, Eisenberg B L, Coleman W B, Kinlaw W B. Lipoprotein lipase links dietary fat to solid tumor cell proliferation. Mol Cancer Ther. 2011 March; 10(3):427-36). Besides the provision of fatty acids for cell proliferation, the impact of the increased fatty acid synthesis versus uptake has remained unknown. In addition to changes in de novo fatty acid synthesis and uptake, there is evidence also for other changes in lipid metabolism, including changes in the expression of phospholipases, COX2, and ELOVL7, an enzyme involved in the elongation of saturated long chain fatty acids (Novel lipogenic enzyme ELOVL7 is involved in prostate cancer growth through saturated long-chain fatty acid metabolism. Tamura K, Makino A, Hullin-Matsuda F, Kobayashi T, Furihata M, Chung S, Ashida S, Miki T, Fujioka T, Shuin T, Nakamura Y, Nakagawa H. Cancer Res. 2009 Oct. 15; 69(20):8133-40.) Besides its role in the production of cholesteryl esters required for steroid hormone synthesis in prostate cancer, the extent of changes in elongation in cancer development by this and by other members of the ELOVL family, its impact on membrane phospholipid composition and its role in cancer development and progression have remained unknown.

Correlations between dietary fatty acids and the risk of developing cancer have been described previously. For example, increased intake of particular n-6 polyunsaturated fatty acids (Godley, P., Campbell, M., Gallagher, P., et al. (1996). Biomarkers of Essential Fatty Acid Consumption and Risk of Prostatic Carcinoma. Cancer Epidemiology, Biomarkers & Prevention 5, 889-895), saturated fatty acids (palmitic acid; Harvei et al., 1997)(myristic acid; Mannisto et al., 2003), and monosaturated fatty acids (palmitoleic acid; Harvei, S., Bjerve, K., Tretli, S., et al. (1997). Prediagnostic level of fatty acids in serum phospholipds: omega-3 and omega-6 fatty acids and the risk of prostate cancer. In. J. Cancer 71, 545-551) have shown association with an increased risk of developing cancer. Furthermore, dietary fatty acids have also been shown to correlate with the aggressiveness of tumors. For example Crowe et al. showed that palmitic acid (saturated fatty acid) was positively correlated with low-grade (less aggressive) prostate cancer, whereas myristic acid (saturated fatty acid) as well as linolenic acid and eicosapentaenoic acid (both n-3 polyunsaturated fatty acids) were positively correlated with high-grade (aggressive) prostate cancer (Crowe, F., Allen, N., Appleby, P., et al. (2008) Fatty acid composition of plasma phospholipids and risk of prostate cancer in a case-control analysis nested within the European Prospective Investigation into Cancer and Nutrition. Am. J. Clin. Nutrition 88: 1353-1363).

Further to these known correlations of dietary fatty acids and cancer prediction/prognosis, we have now found that cancer development is often accompanied by changes in acyl chain length of phospholipids, in particular with a relative increase in the fraction of longer phospholipid species when compared to the fraction of shorter phospholipid species within at least one head group class.

We demonstrate that these changes affect the proliferation and invasiveness of cancer cells. We also show that acyl chain length is modulated by cancer treatment for instance by tyrosine kinase inhibitors, such as imatinib. These findings indicate that membrane phospholipid profiling can be used for the development of diagnostic, prognostic as well as predictive and follow-up tests for assessing the evolution and therapy response of a tumor in a subject. It will also aid in the selection and follow-up of patients benefitting from treatments targeted to the lipid metabolic enzymes themselves, including inhibitors of lipogenesis, elongation and other lipid metabolic processes.

Implementation of the use of such phospholipid profiles as diagnosic/predictive/prognostic biomarkers will lead to a more personalized medicine in which diagnosis and treatment are more interdependent and based on molecular evidence of how a tumor will evolve and respond to a particular treatment. These advances will allow the physician to tailor the treatment to the patient's individual needs. It will also avoid excess of morbidity and side effects due to overtreatment (i.e. sparing the patient from an invasive surgical procedure in case of nonaggressive or too advanced disease), and will optimize the use of available resources.

SUMMARY OF THE INVENTION

An objective of the present invention was to provide an in vitro method for diagnosing and/or predicting the evolution of a tumor in a human subject, said method comprising; determining the relative expression level of intact phospholipid species in at least one head group class in tumor versus normal tissue; and wherein changes in the relative expression level of phospholipid species having the same saturation level but different acyl chain lengths within said at least one head group class, are indicative of a more aggressive elongation phenotype.

In a further embodiment, the in vitro method according to this invention further comprises determining the expression level of at least one mono-unsaturated phospholipid species, and at least one poly-unsaturated phospholipid species; and wherein an increase in relative expression level of said at least one mono-unsaturated phospholipid species and a decrease in relative expression level of said at least one poly-unsaturated phospholipid speices is indicative for a more aggressive lipogenic phenotype; and wherein changes in the relative expression level of phospholipid species having the same saturation level but different acyl chain lengths within at least one head group class, are indicative of a more aggressive elongation phenotype.

In a specific embodiment, the present invention provides an in vitro method according to this invention, wherein a relative increase in longer chain phospholipid species compared to shorter chain phospholipid species within at least one head group class is indicative of a more aggressive elongation phenotype.

In a further embodiment, the phospholipid species are selected from the group comprising; glycerophospholipid, phosphatidic acid, phosphatidylethanolamine, phosphatidylcholine, phosphatidylserine, sphingolipids, cardiolipins and phosphoinositides; preferably phosphatidylcholine, phosphatidylethanolamine, phosphatidylserine and/or phosphoinositide phospholipid species.

In a preferred embodiment, the phospholipid species within said at least one head group class are selected from the list comprising phosphatidylcholine, phosphatidylethanolamine, phosphatidylserine and/or phosphoinositide phospholipid species; in particular phosphatidylserine.

In a further embodiment, the mono-unsaturated phospholipids are phosphatidylcholines (PC) with one or two mono-unsaturated fatty acyl chains, selected from the group comprising; PC28:1, PC30:1, PC30:2, PC32:1, PC32:2, PC34:1, PC34:2, PC36:1, PC36:2, PC38:1, PC38:2, PC40:1 and PC40:2, preferably PC34:1.

In yet a further embodiment, the poly-unsaturated phospholipids are poly-unsaturated phosphatidylcholines (PC), selected from the group comprising; PC32:3, PC34:2, PC34:3, PC34:4, PC36:2, PC36:3, PC36:4, PC36:5, PC36:6, PC38:2, PC38:3, PC38:4, PC38:5, PC38:6, PC38:7, PC40:2, PC40:3, PC40:4, PC40:5, PC40:6, PC40:7, PC40:8, PC42:2, PC42:3, PC424, PC42:5, PC42:6, PC42:7, PC42:8, PC42:9, PC42:10, PC42:11, PC44:2, PC44:3, PC44:4, PC44:5, PC44:6, PC44:7, PC44:8, PC44:9, PC44:10, PC44:11 and PC44:12., preferably PC36:3, PC38:3, PC36:4, PC38:4, PC40:4, PC36:5, PC38:5, PC40:5, most preferably PC36:4 or PC38:4.

In yet another preferred embodiment the mono-unsaturated phospholipids are the mono-unsaturated phosphatidylcholines (PC) PC34:1; and the poly-unsaturated phospholipids are the poly-unsaturated phosphatidylcholines (PC) PC36:4 or PC38:4.

In a preferred embodiment the shorter chain phospholipid species are selected from the list comprising PC30:0, PC32:1, PC34:1, PC32:2, PC34:2, PC34:3, PC36:4, PC36:5, PC38:6; PE32:1, PE34:1, PE34:2, PE36:3, PE36:4, PE36:5, PE38:6, PE38:7, PE40:8, PS34:1, PS36:1, PS34:2, PS36:3, PS36:4, PS38:4, PS38:5, PS38:6 PS40:7; PI32:0, PI34:0, PI30:1, PI34:2, PI36:3, PI36:4, PI38:5 and PI38:6; in particular PC34:1, PC34:2, PE34:1, PE34:2, PE 36:4, PS34:1, PS36:1 PS34:2, PS36:4, PS38:4, PI32:0, PI34:0 and PI36:4.

The in vitro method according to this invention is in particular suitable for tumors selected from the group comprising prostate cancer; renal cancer, such as CCRC; breast cancer; lung cancer; colon cancer; stomach cancer; ovarian cancer; endometrium cancer; liver cancer; oesophagus cancer; bladder cancer; oral cavity cancer; thyroid cancer; pancreas cancer; retina cancer and skin cancer; preferably prostate cancer or renal cancer.

In a further embodiment, the in vitro method according to this invention further comprises measuring the relative expression or phosphorylation/activation of one or more other biomarkers for an aggressive lipogenic phenotype, in tumor sample versus normal, and wherein an increase in relative expression of said one or more other biomarkers is indicative for a more aggressive lipogenic phenotype. In particular said one or more other biomarkers for an aggressive lipogenic phenotype may be selected from the list comprising FASN (fatty acid synthase), ACCA (acetyl CoA carboxylase alpha) and ACLY (ATP citrate lyase) expression.

In particular, the expression level of phospholipid species may be determined via ESI-MS/MS or any other form of mass spectrometry.

The invention further relates to the use of the in vitro method according to the present invention for diagnosing and/or predicting the evolution of a tumor in a subject, including the development of diagnostic, prognostic, predictive and follow-up tests for assessing the evolution and therapy response of a tumor in a subject. It will also aid in the selection and follow-up of patients benefitting from treatments targeted to the lipid metabolic enzymes themselves, including inhibitors of lipogenesis, elongation and other lipid metabolic processes.

Furthermore, the present invention provides the use of an inhibitor of fatty acyl chain length elongation for the treatment of cancer.

Finally, the invention provides a kit for performing the in vitro method according to this invention, said kit comprising; the reagents for the ESI-MS/MS sample preparation of intact phospholipids, in particular an antioxidant, solvents and standards.

BRIEF DESCRIPTION OF THE DRAWINGS

FIGS. 1A-1D are graphs illustrating changes in PL species in a prostate tumor from prostate cancer patients versus normal prostate tissue;

FIGS. 3A-3D are graphs illustrating changes in phospholipid acyl chain length in prostate tumor versus normal prostate tissues;

Referring now to FIGS. 1A-1D, heatmap and clustering of relative changes in PL species in prostate tumor versus normal prostate tissue from 14 prostate cancer patients is illustrated. Phospholipids are ordered according to lipid class (PC, PE, PS and PI). Within each PL class, species are ranked according to the degree of unsaturation and within each subclass of (un)saturation according to their chain length. Light grey to white squares indicate a decrease in PL species in tumor tissue compared to normal tissue, while dark grey to black squares represent an increase as indicated by the scale bar (Log 2). Lined squares indicate missing values. Cluster analysis divided patients in two major groups (A and B) and several subgroups.

FIGS. 2A and 2B illustrate the average of relative changes (log 2) in phospholipid species in prostate tumor versus normal prostate tissue from 13 prostate cancer patients. Phospholipids are ordered according to lipid class (PC, PE, PS and PI). Cluster analysis divided the patients in 2 major groups. Cluster A: 9 patients with lipogenic phenotype (FIG. 2A); Cluster B: 4 patients without lipogenic phenotype (FIG. 2B).

FIGS. 3A-3D illustrate changes in phospholipid acyl chain length in prostate tumor versus normal prostate tissues. To optimally reveal changes in acyl chain length, changes in relative abundance of phospholipid species in tumors and matching normal tissue were plotted relative to the shortest phospholipid species of each subclass of (un)saturation which was set at 0 (Log 2). Light gray to white squares indicate a relative decrease in phospholipid ratio while dark gray to black squares represent an increase as indicated by the scale bar (Log 2). Lined squares indicate missing values.

FIG. 4 illustrates elongation in PS species with 4-7 unsaturations. Changes in relative abundance of phospholipid species in tumors and matching normal tissue were calculated relative to the shortest phospholipid species of each subclass of (un)saturation which was set at 0 (Log 2). The average values of all patients were plotted.

FIGS. 5A and 5B illustrate an elongation profile in PS species with 1-3 unsaturations. Changes in relative abundance of phospholipid species in tumors and matching normal tissue were calculated relative to the shortest phospholipid species of each subclass of (un)saturation which was set at 0 (Log 2). The average values of the patients in cluster D' (A) and cluster D" (B) were plotted. For the patients in cluster D' an additional elongation of PS species with 1-3 unsaturations was seen, which was not seen for the patients in cluster D".

FIG. 6 illustrate overall elongation in PI species. Changes in relative abundance of phospholipid species in tumors and matching normal tissue were calculated relative to the shortest phospholipid species of each subclass of (un)saturation which was set at 0 (Log 2). The average values of all patients were plotted.

FIGS. 7A and 7B illustrate a decrease in elongation in PC and PE species with 1-4 unsaturations for patients in cluster D". Changes in relative abundance of phospholipid species in tumors and matching normal tissue were calculated relative to the shortest phospholipid species of each subclass of (un)saturation which was set at 0 (Log 2). The average values of the patients in cluster D" were plotted.

FIGS. 8A and 8B illustrate an increase in acyl chain length in all head group classes for patient P.8880. Changes in relative abundance of phospholipid species in tumors and matching normal tissue were calculated relative to the shortest phospholipid species of each subclass of (un)saturation which was set at 0 (Log 2).

FIGS. 9A-9D illustrate changes in phospholipid profiles of ccRCC versus matched normal kidney cortex (n=20). Bars represent the average ratio (expressed as log 2) of each species in ccRCC versus control of 20 ccRCC patients. For each head group class (PC, PE, PS and PI: panels A, B, C, D, respectively) lipid species are ordered according to their degree of unsaturation and within each subclass of lipids with an equal number of unsaturations (subclasses separated by the dotted lines), from short to long combined acyl chain length. In the four different head group classes, a marked increase in acyl chain elongation is observed particularly in very long chain polyunsaturated species.

FIG. 10 illustrates changes in phospholipid acyl chain length in exosomes isolated from pre-operative urine samples versus post-operative samples from kidney cancer patients. To optimally reveal changes in acyl chain length, changes in relative abundance of phospholipid species in exosomes isolated from pre-operative urine samples versus post-operative samples were plotted relative to the shortest phospholipid species of each subclass of (un)saturation which was set at 0 (Log 2). Bars represent the average values of 10 patients.

FIGS. 11A-11D illustrate changes in phospholipid acyl chain length in GIST T1 cells treated for 72 hours with 0.1 micromolar imatinib. Lipid profiling was performed in three pairs of samples. The plots show the imatinib/control ratio (expressed as log 2) for different phospholipid head group classes (PC, PE, PI and PS). Lipid species are ordered according to their degree of unsaturation and within each subclass of lipids with an equal number of unsaturations (subclasses separated by the dotted lines), from short to long combined acyl chain length.

FIGS. 12A-12D illustrate changes in phospholipid acyl chain composition in soraphen treated MDA-MB-231 breast adenocarcinoma cells versus control (vehicle treated) cells. Lipid profiling was performed in three pairs of samples. The plots show the soraphen/control ratio (expressed as log 2) for different phospholipid classes. Within each region marked by the dotted lines, the acyl chain length increases from the left to the right. In four different classes, a clear decrease in the longer lipid species is observed when cells are treated with soraphen.

FIGS. 13A-13D illustrate changes in phospholipid acyl chain composition in RCC4 cells treated with soraphen versus control (vehicle treated) cells. Lipid profiling was performed in three pairs of samples. The plots show the soraphen/control ratio (expressed as log 2) for different phospholipid head group classes (PC, PE, PI and PS). Lipid species are ordered according to their degree of unsaturation and within each subclass of lipids with an equal number of unsaturations (subclasses separated by the dotted lines), from short to long combined acyl chain length. In the four different head group classes, a marked inhibition of acyl chain elongation is observed as revealed by the relative increase of shorter lipid species and a concomitant decrease of longer lipid species in soraphen-treated cells.

DESCRIPTION OF THE INVENTION

Figure 1A:
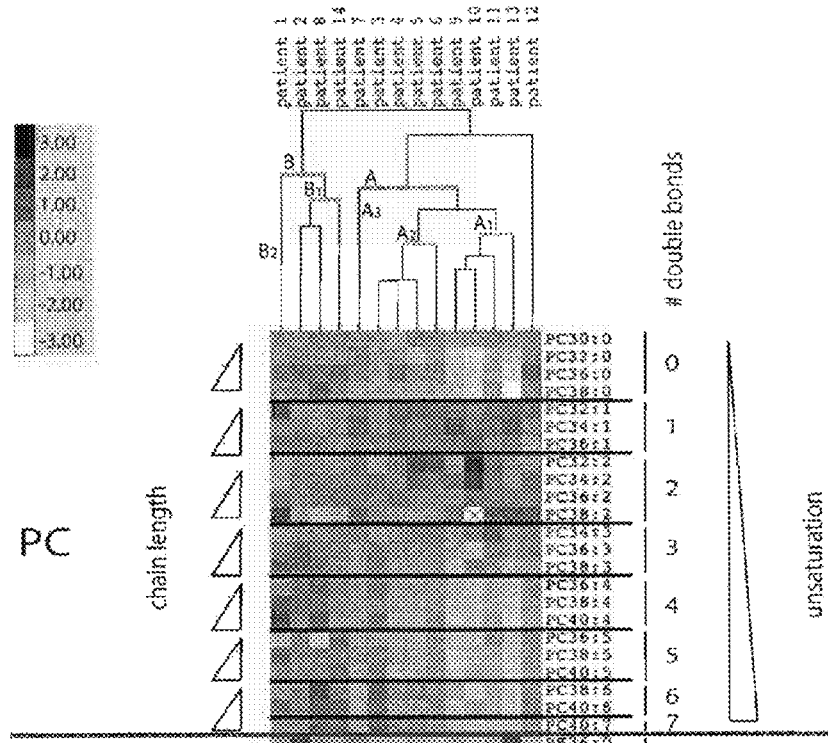

An objective of the present invention was to provide a in vitro method for diagnosing and/or predicting the evolution of a tumor in a subject, said method comprising; determining the relative expression level of intact phospholipid species of one or more head group classes in tumor versus normal tissue; wherein an increase in relative expression level of at least one mono-unsaturated phospholipid and a decrease in relative expression level of at least one poly-unsaturated phospholipid is indicative for a more aggressive lipogenic phenotype; and wherein changes in the relative expression level of phospholipid species having the same saturation level but different acyl chain lengths within the same head group class, are indicative of a more aggressive elongation phenotype.

In a further objective the in vitro method according to this invention further provides determining the expression level of at least 1 mono-unsaturated phospholipid; and at least 1 poly-unsaturated phospholipid, in tumor sample and normal sample; and wherein an increase in relative expression level of said at least one mono-unsaturated phospholipid species and a decrease in relative expression level of said at least one poly-unsaturated phospholipid species is indicative for a more aggressive lipogenic phenotype; and wherein changes in the relative expression level of phospholipid species within at least one head group class, having the same saturation level but different acyl chain lengths are indicative of a more aggressive elongation phenotype.

In a further embodiment the method of the present invention comprises determining the relative expression level of at least 2, 3, 4, 5, 6, 7, 8, 9, 10, 11, 12, 13, 14, 15, 16, 17, 18, 19 or 20 mono-unsaturated phospholipids.

In yet a further embodiment the method of the present invention comprises determining the relative expression level of at least 2, 3, 4, 5, 6, 7, 8, 9, 10, 11, 12, 13, 14, 15, 16, 17, 18, 19 or 20 poly-unsaturated phospholipids.

In the context of the present invention, any suitable lipid extraction method may be used, such as for example Hybrid Solid Phase Extraction (SPE)-Phospholipid technology, wherein phospholipids are extracted based on a Lewis Acid-Base interaction between zirconia atoms coated to silica beads and the phosphate moiety of phospholipids. In a particular embodiment, the lipids are extracted on a medium comprising a hydrophilic modified styrene based polymer. Briefly, lipids are released from the tumor (cell or tissue) sample and separated from the cellular material using centrifugation step. The thus obtained supernatant is applied on said polymer, washed by a water liquid and consequently by a water:alcohol liquid whereby the lipid fraction is subsequently eluted by an alcohol:acetonitrile liquid. In the above-mentioned process, preferably HLB SPE (hydrophilic lipophilic balanced Solid-Phase Extraction) is used, wherein the water:alcohol is water: methanol, and the alcohol:acetonitrile is methanol: acetonitrile.

HLB SPE is a hydrophilic modified styrene based polymer developed for the solid phase extraction of a broad range of (pharmaceutical) compounds from aqueous samples. We have now found that HLB SPE is also very suitable for the extraction of phospholipids, and have further optimized the existing protocol as evident from the examples that follow hereinafter.

Thus, in a preferred embodiment, the present invention provides an in vitro method for diagnosing and/or predicting the evolution of a tumor as defined herein, wherein the step of isolating intact phospholipid species comprises obtaining said phospholipids by an HLB SPE-based method, more in particular by the method as detailed in the examples that follow hereinafter.

"m/z" is Mass over charge [I. T. Jolliffe, Principal component analysis, 2nd ed. New York: Springer, 2002. and M. Ringn'er, "What is principal component analysis?" Nat Biotechnol, vol. 26, no. 3, pp. 303-4, March 2008.]

An "assay" in the meaning of this application is an analysis or procedure to determine the presence or absence of one or more molecular species in an organism or an organic sample. A quantitative assay also measures the quantity of its target analyte in the sample.

The "total ion current" in the meaning of present invention is the sum of the separate ion currents carried by the different ions contributing to the spectrum [A. D. McNaught and A. Wilkinson, Compendium of chemical terminology: IUPAC recommendations, 2nd ed. Oxford: Blackwell Science, 1997. [Online].Available: http://goldbook.iupac.org/index.html]. From a mathematical standpoint, the sum of all ion counts in a mass spectrum irrespective of ion species, or the integral over the mass spectral profile.

"Ionization efficiency" in the meaning of this application is the ratio of the number of ions formed to the number of electrons or photons used in an ionization process [A. D. McNaught and A. Wilkinson, Compendium of chemical terminology: IUPAC recommendations, 2nd ed. Oxford: Blackwell Science, 1997. [Online]. Available: http://goldbook.iupac.org/index.html].

In this application a "mass" or "m/z" means" a mass to charge ratio, and a "mass range" or a "m/z range" means a range for the mass to charge ratio. A linear dynamic range is the range over which ion signal is linear with the analyte concentration. Mass accuracy is the ratio of the m/z measurement error or to the true m/z. The mass resolving power is the measurement of the ability to distinguish two peaks of slightly different m/z.

Spectrometry is the spectroscopic technique used to assess the concentration or amount of a given chemical (atomic, molecular, or ionic) species. In this case, the instrument that performs such measurements is a spectrometer, spectrophotometer, or spectrograph.

A mass spectrometer is an apparatus for the determination of the elemental composition of an analyte sample or molecule and/or for elucidating the chemical structures of molecules, such as peptides and other chemical compounds. The mass spectrometry principle consists of ionizing chemical compounds of an analyte to generate charged molecules or molecule fragments, transporting such ions by a potential (e.g. under an either static or dynamic magnetic or electric field) and measurement of their mass-to-charge (m/z) ratios.

"Electrospray ionization" (ESI) is a technique used in mass spectrometry to produce ions. It is especially useful in producing ions from macromolecules because it overcomes the propensity of these molecules to fragment when ionized. Mass spectrometry using ESI is called electrospray ionization mass spectrometry (ESI-MS) or, less commonly, electrospray mass spectrometry (ES-MS). Electrospray ionization is the ion source of choice to couple liquid chromatography with mass spectrometry. The analysis can be performed online, by feeding the liquid eluting from the LC column directly to an electrospray, or offline, by collecting fractions to be later analyzed in a classical nanoelectrospray-mass spectrometry setup.

As used herein a "tumor" is defined as an abnormal growing mass of cells. Tumors useful for the present invention include but are not limited to prostate cancer; renal cancer, such as CCRC; breast cancer; lung cancer; colon cancer; stomach cancer; ovarian cancer; endometrium cancer; liver cancer; oesophagus cancer; bladder cancer; oral cavity cancer; thyroid cancer; pancreas cancer; retina cancer and skin cancer; preferably prostate cancer or renal cancer.

With a "tumor sample" is meant a sample taken from a cancer patient either prior to or after removal of the tumor from the subject bearing said tumor. Said sample can be taken directly from the tumor, e.g. a biopsy. It may also include a body fluid-derived sample, such as for example blood, serum, or urine; including isolates obtained from said body fluid-derived samples, such as for example exosomes.

With a normal sample is meant a sample obtained for use in determining base-line expression levels. Accordingly, a normal sample may be obtained by a number of means including from non-cancerous cells or tissue e.g., from cells surrounding a tumor or cancerous cells of a subject; from subjects not having a cancer; from subjects not suspected of being at risk for a cancer; or from body fluids, cells or cell lines derived from such subjects. A normal sample also includes a previously established standard, such as a previously characterized cancer cell line. Accordingly, any test or assay conducted according to the invention may be compared with the established standard and it may not be necessary to obtain a normal sample for comparison each time.

A sample can be any tissue, cell, cell extract, serum, whole blood, plasma concentrate, exosome fraction, a precipitate from any fractionation of the plasma/blood, a body fluid, etc isolated from a subject such as for example a sample isolated from a subject having cancer or from a healthy volunteer. A "sample" may also be a cell or cell line created under experimental conditions, that is not directly isolated from a subject. A subject can be a human, rat, mouse, non-human primate, feline, etc.

For example, exosomes could be extracted from a urine, blood or serum sample from a cancer patient. Since the membranes of said exosomes are a representation of the cell membrane of the cancer cells from which they arrive, phospholipid profiling of these exosomes is a good alternative for phospholipid profiling from cancer tissue directly and more importantly a much less invasive method. This makes it much easier to follow the progression of a tumor over time, without having to take biopsies of the tumor each time. Said exosomes can for example be isolated making use of lab-on-chip technology, allowing also subsequent analysis of the phospholipid profiles, thereby allowing high-throughput screening. In the latter exosomes (microvesicles) can be isolated by selective precipitation, affinity purification or by differential centrifugation according to previous publications (Valadi H, Ekstrom K, Bossios A, Sjostrand M, Lee J J, Lotvall J O. Exosome-mediated transfer of mRNAs and microRNAs is a novel mechanism of genetic exchange between cells. Nat Cell Biol 2007; 9:654-659—Zhang Y, Liu D, Chen X, Li J, Li L, Bian Z, Sun F, Lu J, Yin Y, Cai X, Sun Q, Wang K, Ba Y, Wang Q, Wang D, Yang J, Liu P, Xu T, Yan Q, Zhang J, Zen K, Zhang C Y. Secreted monocytic miR-150 enhances targeted endothelial cell migration. Mol Cell 2010; 39:133-144.). Briefly, after removing cells and other debris by centrifugation at 2000 g, and 17000 g, the supernatant are centrifuged at 200,000 g for 70 min (all steps were performed at 4° C.). Exosomes are collected from the pellet and resuspended in PBS. The presence of exosomes after ultracentrifugation are determined with flow cytometry. To confirm that the vesicles are of the correct size, flow cytometry gates were set using 1 micron beads (Invitrogen), yielding microvesicles for use on microfluidic chips as described herein below.

By using the in vitro method of the present invention, one is able to predict the presence of a tumor, and the evolution of a tumor, i.e. the potential of a tumor to evolve into an aggressive tumor phenotype or to predict or follow-up the potential of a tumor to respond to anti-cancer therapy. Said anti-cancer therapy including any therapy known from the art, such as for example, but not limited to chemotherapy, molecular targeted therapies, lipid metabolism targeted therapies, immunotherapy, radiotherapy, . . . .

With a tumor having an aggressive lipogenic phenotype is meant a tumor which endogenously produces fatty acids de novo and renders the patient with a poorer prognosis i.e. a tumor which is less responsive to anti-cancer therapy and/or having a higher potential to progress or to metastasize compared to a tumor rendering the patient with a good survival prognosis.

With a tumor having an elongation phenotype is meant a tumor which shows changes in the individual or combined acyl chain length of any lipid species which renders that tumor more or less aggressive in terms of cell proliferation, invasiveness, etc. In particular said changes relate to a relative increase in longer phospholipid species compared to shorter phospholipid species within one or more head group classes; more in particular in one or more of the head group classes selected from phosphatidylcholine, phosphatidylethanolamine, phosphatidylserine and/or phosphatidylinositol phospholipid species, in particular in the phosphatidylserine phospholipid class.

Phospholipids are a class of lipids that are a major component of cell membranes and that can form lipid bilayers. Phospholipids consist of a hydrophilic head group and a hydrophobic tail. The head group typically contains, a phosphate group and a simple organic molecule such as for example choline in phosphatidylcholine, and is bound through glycerol to the hydrophobic tail that typically consists of a diglyceride. A diglyceride consists of 2 fatty acid chains, covalently bound to a glycerol molecule through ester linkages. A fatty acid is a carboxylic acid having an unbranched aliphatic tail of at least 4 carbon atoms, which is either saturated or unsaturated, depending on the presence of double bonds. Saturated fatty acids are fatty acids with no double bonds in their aliphatic tail, mono-unsaturated fatty acids are fatty acids having exactly one double bond in their aliphatic tail, and poly-unsaturated fatty acids have 2, 3, 4, 5, 6, 7 or more double bonds in their aliphatic tail. Based on the composition of the hydrophilic head group, phospholipids are further classified in head group classes such as glycerophospholipid, phosphatidic acid, phosphatidylethanolamine, phosphatidylcholine, phosphatidylserine, sphingolipids, cardiolipins and phosphoinositides. As will be apparent from the examples hereinafter, within the methods of the present invention, the differences in elongation are determined within such a head group class.

The phospholipids according to the present invention are in particular selected from the group comprising; glycerophospholipid, phosphatidic acid, phosphatidylethanolamine, phosphatidylcholine, phosphatidylserine, sphingolipids, cardiolipins and phosphoinositides; more in particular phosphatidylethanolamine, phosphatidylcholine, phosphatidylserine, and phosphoinositides.

By expression level of phospholipids is meant the levels of intact phospholipids as determined by any suitable method, such as for example analyzed by ESI-MS/MS. In said methodology, the phospholipids are identified based on the intensity of the ionised species, expressed as absolute values determined relative to lipid standards, or as mole percentage or the % intensity level of individual phospholipids, versus the total intensity level of all phospholipids measured.

With the relative expression level of phospholipids is meant the difference in expression level of phospholipids in a tumor sample compared to the expression level of phospholipids in a normal sample. In some embodiments, the relative expression level may be determined at different time points, e.g. before, during, and after therapy. The relative expression level may be expressed in any suitable way such as for example as log 2.

The relative expression level of phospholipids is considered to be increased if the log 2 value is higher than about 0, whereas it is considered to be decreased if the log 2 value is lower than about 0. In a further embodiment the relative expression level of fatty acids is considered to be increased if the log 2 value is higher than about 0.1; 0.2; 0.3; 0.4; or 0.5; and the relative expression level of fatty acids is considered to be decreased if the log 2 value is lower than about −0.1; −0.2; −0.3; −0.4 or −0.5.

In an alternative embodiment of the present invention, the change in phospholipids composition is scored by determining the ratio of longer versus shorter acyl chain or combined acyl chain length in for example species with the same degree of unsaturation, wherein a shift towards longer (or in some cases shorter) acyl chain length is indicative of a more aggressive elongation phenotype. Also, the change in phospholipids composition may be scored by determining the ratio of mono-unsaturated versus poly-unsaturated phospholipids in a sample, wherein an increase in the ratio of mono-unsaturated versus poly-unsaturated phospholipids in a tumor sample versus a normal sample is indicative for a more aggressive lipogenic phenotype of the tumor.

In a further embodiment the mono-unsaturated phospholipids according to the present invention are mono-unsaturated phosphatidylcholines (PC), selected from the group comprising; PC30:1, PC32:1, PC34:1, PC36:1 and PC38:1, preferably PC34:1.

In a further embodiment, the poly-unsaturated phospholipids are poly-unsaturated phosphatidylcholines (PC), selected from the group comprising; PC32:3, PC34:2, PC34:3, PC34:4, PC36:2, PC36:3, PC36:4, PC36:5, PC36:6, PC38:2, PC38:

3, PC38:4, PC38:5, PC38:6, PC38:7, PC40:2, PC40:3, PC40:4, PC40:5, PC40:6, PC40:7, PC40:8, PC42:2, PC42:3, PC424, PC42:5, PC42:6, PC42:7, PC42:8, PC42:9, PC42:10, PC42:11, PC44:2, PC44:3, PC44:4, PC44:5, PC44:6, PC44:7, PC44:8, PC44:9, PC44:10, PC44:11 and PC44:12; preferably PC36:3, PC38:3, PC36:4, PC38:4, PC40:4, PC36:5, PC38:5, PC40:5; and most preferably PC36:4 and/or PC38:4.

In a preferred embodiment, the mono-unsaturated phosholipids are the mono-unsaturated phosphatidylcholines (PC) PC34:1; and the poly-unsaturated phospholipids are the poly-unsaturated phosphatidylcholines (PC) PC36:4 and/or PC38:4.

In a particular embodiment of this invention, the shorter chain phospholipid species are all measurable phospholipid species with the same head group and equal number of unsaturations but with shorter than average (combined) acyl chain lengths. In a more particular embodiment of this invention, the shorter chain phospholipid species are selected from the list comprising PC30:0, PC32:1, PC34:1, PC32:2, PC34:2, PC34:3, PC36:4, PC36:5, PC38:6; PE32:1, PE34:1, PE34:2, PE36:3, PE36:4, PE36:5, PE38:6, PE38:7, PE40:8, PS34:1, PS36:1, PS34:2, PS36:3, PS36:4, PS38:4, PS38:5, PS38:6 PS40:7; PI32:0, PI34:0, PI30:1, PI34:2, PI36:3, PI36:4, PI38:5 and PI38:6; in particular PC34:1, PC34:2, PE34:1, PE34:2, PE 36:4, PS34:1, PS36:1 PS34:2, PS36:4, PS38:4, PI32:0, PI34:0 en PI36:4.

In a further embodiment, in addition to determining the expression of phospholipids, the relative expression level of other biomarkers for an aggressive lipogenic phenotype may be determined, such as for example, but not limited to, FASN (fatty acid synthase), ACCA (acetyl CoA carboxylase alpha) and ACLY (ATP citrate lyase) expression or phosphorylation/activation. A tumor having an aggressive lipogenic phenotype may than for example be identified by an increase in relative expression level of mono-unsaturated phospholipids, a decrease in relative expression level of poly-unsaturated phospholipids, and an increase in expression of one or more other biomarker for an aggressive lipogenic phenotype. Alternatively, a tumor having an aggressive lipogenic phenotype may for example be identified by an increased ratio of mono-unsaturated versus poly-unsaturated phospholipids in the tumor sample compared to the normal sample, and an increase in expression of one or more other biomarker for an aggressive lipogenic phenotype.

The invention further relates to the use of the in vitro method according to the present invention for diagnosing and/or predicting the evolution of a tumor in a subject.

The data presented in the examples hereinafter indicate that the elongation phenotype is involved in the development, invasiveness and aggressiveness of tumors and that inhibitors of said elongation phenotype could be beneficial in the treatment of cancer, in particular those types of cancer in which elongation is involved. The invention therefore further provides the use of an inhibitor of fatty acyl chain length elongation for the treatment of cancer.

Finally, the invention provides a kit for performing the in vitro method according to this invention, said kit comprising the reagents for sample preparation of phospholipids for lipid analysis, in particular tools for body fluid fractionation, tissue homogenization, lipid extraction, an antioxidant, solvents and/or standards.

In a particular embodiment said kit comprises a microfluidic chip, and a coated surface for the immobilization of microvesicles to a surface coated with molecules or agents having an affinity for said microvesicles or being capable of binding microvesicular particles.

Any molecule which has an affinity for microvesicles suitable for coating the selected surface material can be used. With a molecule having an affinity for microvesicles is meant that such molecule is capable of binding covalently or non-covalently to a molecule present on a microvesicle. Preferably said molecule present on a microvesicle is a membrane-bound molecule. Preferably, molecules having a high affinity for a microvesicle are used. Preferably, affinity is expressed as a dissociation constant. Preferably, molecules having a dissociation constant lower than 0.1 nM for microvesicles are used, more preferably lower than 10 nM. More preferably, molecules having a dissociation constant lower than $10^{-15}$ M for microvesicles are used. In another preferred embodiment, an affinity for a microvesicle is used with a dissociation constant in a range between 0.1-10 nM. Methods of determining affinity are known in the art. Preferably, a method is used as described in Johnson et al. Journal of Molecular Biology 368 (2): 434-449.

Any surface that is suitable for immobilization using coatings having an affinity for microvesicles can be used Preferred surfaces are made of material comprising glass, mica, plastic, metal or ceramic materials. There are various methods known for coating surfaces having affinity for (glyco)-proteins, cell membranes or biomolecules in general. Typically, these methods use a reactive group which binds covalently or non-covalently to a certain biomolecule. For example, slides coated with aminopropylsilane are used for non-covalent adsorption of protein. Epoxysilane coated slides are reactive with lysine, arginine, cysteine and hydroxyls at pH 5-9. Aldehyde coated slides are reactive with lysine and arginine where pH 7-10 drives Schiff's base reaction. A skilled person will know how to select the right coating suitable for use in combination with the selected surface material and test the affinity for microvesicles.

The resulting coated surface is put into contact with microvesicles by applying a laminar flow to a fluid comprising said microvesicles. Said fluid can be any fluid that is compatible with microvesicles. With compatible is meant that the integrity of the microvesicles remains intact, which means that at least phospholipids used in the methods of the present invention are present within the microvesicles. Preferably said fluid comprises plasma, cell culture medium, phosphate buffered saline (PBS), phosphate buffered potassium, or 4-(2-hydroxyethyl)-1-piperazineethanesulfonic acid (HEPES).

A laminar flow is a flow regime characterized by high momentum diffusion, low momentum convection, pressure and velocity independent from time. Said laminar flow is characterized by a Reynolds number of less than 2000 and higher than 0. Preferably, laminar flows with a Reynolds value between 0 and 1000, more preferably between 0 and 500 and most preferably between 0 and 100. A skilled person will know how to achieve a laminar flow. Any method capable of applying a fluid in a laminar flow to said coated surface can be used. Preferred is a laminar flow which is linear in one direction. Preferred is a laminar flow that optimizes the contact area, contact time and flow speed to the functionality of the fluidic device. Further preferred is a laminar flow through a channel comprising a functionalized wall.

Preferably, a method is used wherein the affinity for the microvesicles is specific. An advantage of a specific affinity is that binding of undesired molecules or particles is reduced. Preferred methods are methods in which an affinity linker is bound covalently or non-covalently to the surface. An affinity linker is a molecule that is capable to covalently or non-covalently bind to a binding partner, resulting in a complex between said affinity linker and said binding partner. Said binding partner can be a molecule capable of binding to a microvesicle or it can be a molecule present on the microvesicle that can directly interact with said affinity linker. Examples of affinity linkers and their binding partners are; Streptavidin or avidin and biotin; an antibody and antigen; a ligand and receptor, lectin and saccharide, protein A and/or protein G-immunoglobulin constant region, and Tag peptide sequence and Tag antibody. The terms affinity linker and binding partner refer to their function. Therefore, depending on how the above mentioned affinity linker-binding partner combinations are used, the terms are exchangeable. For example a biotin can be an affinity linker if it is bound to the surface or it can be a binding partner when it is bound to the microvesicle. Any method to bind an affinity linker to a surface can be used. Methods to bind an affinity linker to a coated surface differ depending on the material of surface and the nature of the affinity linker. A skilled person will be able to select the correct method suitable for the type of surface material and affinity linker of choice. Methods to bind an affinity linker to a surface are known to a skilled person. Methods to bind antibodies to metal or silicon surface are well known in the art. Preferred methods are described in Bioelectrochemistry Volume 66, Issues 1-2, April 2005, Pages 111-115. Methods to bind antibodies to glass surface are also known and described in J Colloid Interface Sci. 2002 Aug. 1; 252(1):50-6. In a particular embodiment the affinity linkers are selected from the group consisting of antibody species, proteins, aptamers, surfaces selectively restricting microvesicles from passage, and surfaces with selective adhesion to microvesicles; wherein the proteins are particularly selected from the list comprising lectin, or other sugar binding compounds; and wherein the lectin is particularly selected from the group comprising GNA, NPA, Concanavalin A, or cyanovirin.

In a more particular embodiment, said laminar flow is applied using microfluidics. The term microfluidics refers to devices, systems, and methods for the manipulation of fluid flows with characteristic length scales in the micrometer range up to 1 millimeter (see for a more complete overview: Manz, A. and Becker. H. (Eds.), Microsystem Technology in Chemistry and Life Sciences, Springer-Verlag Berlin Heidelberg New York, ISBN 3-540-65555-7). An advantage is that microfluidic systems possess the capability to execute operations more quickly than conventional, macroscopic systems, while consuming much smaller amounts of chemicals and fluids.

In a particular embodiment of the present invention said laminar flow is created using a microfluidic chip. Preferably said microfluidic chip comprises at least one microfluidic channel with an inlet and an outlet, wherein said at least one microfluidic channel has at least one gap at a surface of said microfluidic chip enabling contact between said at least one channel and a surface. An advantage of said microfluidic chip is that it enables direct contact between a fluid in said microfluidic channel and a surface. Preferably said inlet and/or said outlet are positioned at a different surface of said microfluidic chip than the surface comprising said gap in said microfluidic channel. An advantage thereof is that this enables clamping between said microfluidic chip and said surface, while maintaining access to said inlet and/or outlet. In a preferred embodiment, holes are provided in said microfluidic chip, enabling screws or other means to attach a surface to said microfluidic chip. An advantage thereof is that a surface can be attached to said microfluidic chip to achieve a contact which prevents leakage of a fluid from said microfluidic channel. An advantage of using a microfluidic channel is that the geometry of the channel enables a controllable inducement of a laminar flow. Preferably, said channel has a height which is less than 1 mm. An advantage thereof is that the surface to volume ratio of said fluid over said coated surface is optimized. In another preferred embodiment, the channel height above the coated area is less than the channel height in other parts of the microfluidic device. An advantage thereof is that the surface to volume ratio of said fluid over the coated area is optimized, while maintaining a flow through. More preferably, said channel height is less than 0.5 mm. An advantage thereof is that this height is optimal for fluids having a viscosity of plasma. Preferably, said channel has a width of less than 1 mm. An advantage thereof is that this results in a minimal contact area of said coated surface which is in contact said fluid. Preferably, said minimal contact area is smaller than said coated surface area.

Preferably, said minimal contact area is between 100 and 10000 square micrometer. In a preferred embodiment, said minimal contact area is less than 1 square millimeter. An advantage thereof is that this limits the surface area inspection time and increases the concentration of collected vesicles per surface area. More preferably, said minimal contact area is between 1 square micrometer and 0.1 square millimeter.

As is known to the skilled artisan, the aforementioned channels may further comprise a filter which allows particles smaller than a microvesicle to pass through. In this method, microvesicles are collected on the surface of said filter, a change of flow direction is then applied to re-suspend said microvesicles. This method further comprises a step of resuspending said microvesicles in a fluid before allowing said fluid comprising said microvesicles to contact said coated surface. Accordingly, in an even further embodiment the microfluidic chip as used herein comprises a pumping system. Any system suitable of pumping fluid inside a microfluidic circuit can be used. Examples are described in PHYSICS AND APPLICATIONS OF MICROFLUIDICS IN BIOLOGY David J. Beebe, Glennys A. Mensing, Glenn M. Walker Annual Review of Biomedical Engineering, August 2002, Vol. 4, Pages 261-286.

When using microfluidic chips in the methods of the present invention, detection of microvesicles may be done using imaging techniques. An advantage of this is that this allows measurements of one or more parameters comprising but not limited to particle geometry, shape, roughness, light scattering or dimensions of microvesicles or the presence of molecules on the surface of or inside microvesicles can be determined. Any method of imaging can be used in the method. Preferred methods of imaging comprise fluorescence microscopy, including internal reflection fluorescence microscopy, electron microscopy (EM), confocal microscopy, light scattering or surface plasmon microscopy, Raman spectroscopy, ellipsometry/reflectometry, infrared spectroscopy or atomic force microscopy (AFM), or combinations thereof.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. Other embodiments will occur to the person skilled in the art in light of these examples.

Example 1

Phospholipid Profiling in an Extended Group of Prostate Tumor Patients Making Use of PC, PE, PS and PI Profiles Methodology
Tissue Collection Prostate tumor tissues and matching normal samples were obtained from patients who had undergone a radical retropubic prostatectomy for localized prostatic carcinoma. Prostate tissue specimens were taken using a 6 or 8 mm diameter punch biopsy instrument. Samples were snap-frozen in liquid nitrogen and stored at −80° C. for lipid, protein and RNA extractions. Normal and tumor tissues were identified by histological analysis of areas adjacent to the tissue that were embedded in Tissue-Tek OCT (Miles Inc, Westhaven, Conn.) Serial sections were processed for hematoxylin and eosin staining. The cancer samples were evaluated for their Gleason scores and the percentage of cancer they contain was estimated.

Determination of DNA Concentration

Determination of the DNA concentration is used to normalize the amount of standards and running solution added to the samples used for lipid analysis. Samples were sonicated and diluted in homogenization buffer (5×10-2M Na2HPO4/NaH2PO4 buffer Ph 7.4; 2M NaCl and 2×10-3 M EDTA). Herring sperm DNA (Promega, Madison, Wis.; 0-5 μg DNA/125 μl) was used to create a standard curve by making different dilutions in homogenization buffer. Next, samples were incubated for one hour at 37° C. to improve lysis. Thereafter, 2 μg/ml Hoechst 33258 reagent (Calbiochem, La Jolla, Calif.) was added.

DNA content of the samples and the herring sperm DNA were measured using a fluorimeter (Fluostar SLT, BMG Labtech, Offenburg, Germany). Excitation: 355 ηm; emission: 460ηm. The DNA content of each sample was calculated based on the data of the standard curve.

Lipid Extraction

Lipid extracts of the samples were made by homogenizing approximately 40 mg of tissue in 800 μl PBS with a Dounce homogenizer. An aliquot of 100 μl was set aside for DNA analysis. The remaining 700 μl was transferred to a glass tube with Teflon liner and 900 μl N HCl:CH3OH 1:8 (v/v), 800 μl CHC13 and 500 μg of the antioxidant 2,6-di-tert-butyl-4-methylphenol (BHT) (Sigma, St. Louis, Mo.) were added. The appropriate lipid standards were added based on the amount of DNA of the original sample (per mg DNA: 150 ηmol PC 26:0; 50 ηmol PC 28:0; 150 ηmol PC 40:0; 75 ηmol PE 28:0; 8.61 ηmol PI 25:0 and 3 ηmol PS 28:0). After mixing for 5 min in a rotary shaker and phase separation (high speed centrifugation at 17300 g, for 5 min at 4° C.), the lower organic fraction was collected using a glass Pasteur pipette and evaporated using a Savant Speedvac spd111v (Thermo Fisher Scientific, Waltham, Mass.). The remaining lipid pellet was stored at −20° C.

Mass Spectrometry

For mass spectrometry (MS), lipid pellets were reconstituted in running solution (CH3OH:CHC13:NH4 OH; 90:10:1.25, v/v/v) depending on the amount of DNA of the original tissue sample (1 μl running solution/1 μg DNA). PL species were analyzed by electrospray ionization tandem mass spectrometry (ESI-MS/MS) on a hybrid quadrupole linear ion trap mass spectrometer (4000 QTRAP system; Applied Biosystems, Foster City, Calif.) equipped with an Advion TriVersa robotic nanosource for automated sample injection. (Advion Biosciences, Ithaca, N.Y.). Before measurement, samples were diluted in running solution. A dilution of 1/30 was used for measurement of the phosphatidylcholine (PC), phosphatidylserine (PS), phosphatidylinositol (PI) species and phosphatidylethanolamine (PE) species.

PL profiles were recorded in positive and negative ion scan mode at a collision energy of 50 eV for precursor (prec.) 184, 35 eV for neutral loss (nl.) 141, −40 eV for nl. 87 and −55 eV for prec. 241 for PC, PE, PS and PI species respectively. For quantification of individual species the system was operated in the MRM mode. Typically, a 3 min period of signal averaging was used for each spectrum. Data were corrected for carbon isotope effects and are expressed as the percentage of total measurable PL species of the same PL family. Only the PL species which account for more than 0.1% of the total amount of measured phospholipids of the same family are shown in the graphs.

Cluster Analysis

Clustering analysis was carried out by using an average linkage clustering algorithm of the Cluster 3.0 software [Eisen, M. B., P. T. Spellman, P. O. Brown, and D. Botstein, Cluster analysis and display of genome-wide expression patterns. Proc Natl Acad Sci USA, 1998. 95(25): p. 14863-8.]. The clustering results were visualized using the Java TreeView 1.1.5. software [Saldanha, A. J., *Java Treeview—extensible visualization of microarray data. Bioinformatics*, 2004. 20(17): p. 3246-8.].

Results
Characteristics of Tumor Specimens

To study changes in PL profiles in cancer tissue versus normal tissue and among tumor tissues of individual patients, approximately 40 mg of prostate tumor tissue and adjacent normal prostate tissue from 14 prostate cancer patients, who had undergone a radical retropubic prostatectomy for localized prostatic carcinoma. All tumor tissues were verified by histological examination to consist for at least 80 percent of tumor tissue. All tumors had a Gleason grade of 3+3 or 3+4 (Table 1).

TABLE 1

Percentage of cancer tissue and Gleason grade of each tumor sample.

| Patient ID | % tumor | Gleason grade |
|---|---|---|
| Patient 1 | 100 | 3+4 |
| Patient 2 | 95 | 3+4 |
| Patient 3 | 100 | 3+3 |
| Patient 4 | 90 | 3+3 |
| Patient 5 | 95 | 3+3 |
| Patient 6 | 95 | 3+3 |
| Patient 7 | 95 | 3+4 |
| Patient 8 | 80 | 3+3 |
| Patient 9 | 90 | 3+3 |
| Patient 10 | 85 | 3+3 |
| Patient 11 | 80 | 3+3 |
| Patient 12 | 85 | 3+3 |
| Patient 13 | 85 | 3+4 |
| Patient 14 | 80 | 3+3 |

Optimization of the Phospholipid Profiling Procedure

To look at intact PL species we used a mass spectrometry-based approach that was developed in house in collaboration with Prof. R. Derua and Prof. E. Waelkens (Department of Molecular Cell Biology, K. U. leuven). This procedure was based on a protocol described by Brügger et al [Brugger, B., G. Erben, R. Sandhoff F. T. Wieland, and W. D. Lehmann, *Quantitative analysis of biological membrane lipids at the low picomole level by nano-electrospray ionization tandem* mass spectrometry. *Proc Natl Acad Sci USA,* 1997. 94(6): p. 2339-44.] and Milne et al [Milne, S., P. Ivanova, J. Forrester, and H. Alex Brown, *Lipidomics: an analysis of cellular lipids by ESI-MS. Methods,* 2006. 39(2): p. 92-103.] and was adapted for use on an ABI 4000 QTRAP mass spectrometer equipped with a Triversa robotic nanoflow/ion source device for automated sample injection.

As this protocol was developed for PL analysis of cultured cells, we adapted it for use on clinical samples. Briefly, the homogenization procedure was optimized by varying the amount of starting material and by modifying the procedure (number of strokes) for Dounce homogenization. The MS procedure was optimized by varying the dilution of the lipid extracts.

Phospholipid Profiling of Prostate Cancer Tissues and Matching Normal Tissues

In order to detect individual classes of phospholipids directly from total lipid extracts in a shotgun approach, different precursor ion and neutral loss scans were run in a tandem mass spectrometric (MS/MS) analysis. This approach enables to focus on specific classes of lipids, reducing the complexity of the spectra, and eliminates baseline noise.

Four major PL classes were analyzed: PC, PE, PS and PI. PC species were detected in positive ion mode in a precursor scan for m/z 184, corresponding to the phosphocholine head group peak after fragmentation in MS/MS mode. PE species were detected by collision-induced decomposition in positive ion mode yielding an ion corresponding to the nl. of phosphoethanolamine. PS and PI were measured in negative ion mode scan for nl.87 and prec. 241, respectively.

Quantification of species was done in multiple reaction monitoring (MRM) mode, after isotope correction, focusing on the most abundant PL species. These species are listed in Table 2.

For optimal identification of changes in acyl chain length and degree of unsaturation, amounts of lipid species were not expressed in absolute values but rather as the percentage of all measurable species within one class of phospholipids (e.g. PC). To avoid errors due to differences in ionization efficiency, differences in the percentages were indicated as a ratio of values in cancer tissue compared to matching normal tissue. A log 2 scale was used to equalize differences in both directions (increase and decrease). To avoid errors due to background noise species accounting for less than 0.1% of the total intensity of all species of one PL family were not taken into account.

Figure 1B:
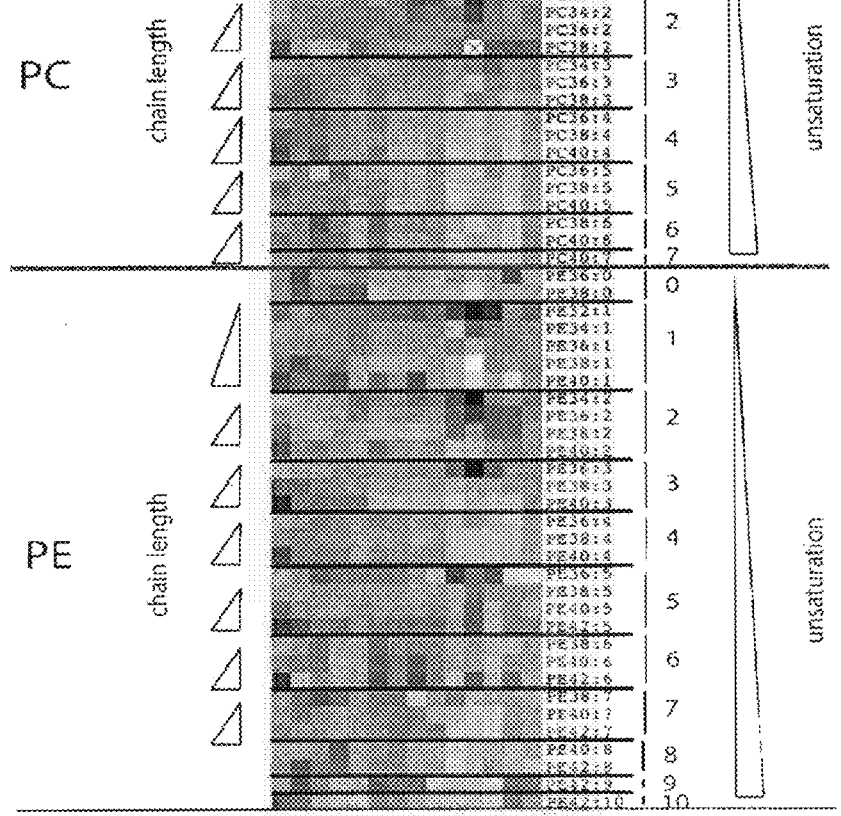

The grey tone heatmap of FIG. 1 shows for instance relative changes in PL species in prostate tumor versus normal prostate tissue from the 14 prostate cancer patients. Marked differences were observed in PL profiles in 13 out of 14 patients. Interestingly, different patterns of changes were observed among different patients. Some changes (e.g. an increase in PS 40:8) were observed in all patients. Most other changes were restricted to specific subsets of patients (e.g. increase in PE 38:0). To better reveal differences and similarities in PL profiles among the different patients, cluster analysis was performed. This revealed recurrent changes and divided the patients in 2 major groups, which can be further divided in subgroups.

Figures 2A, 2B:
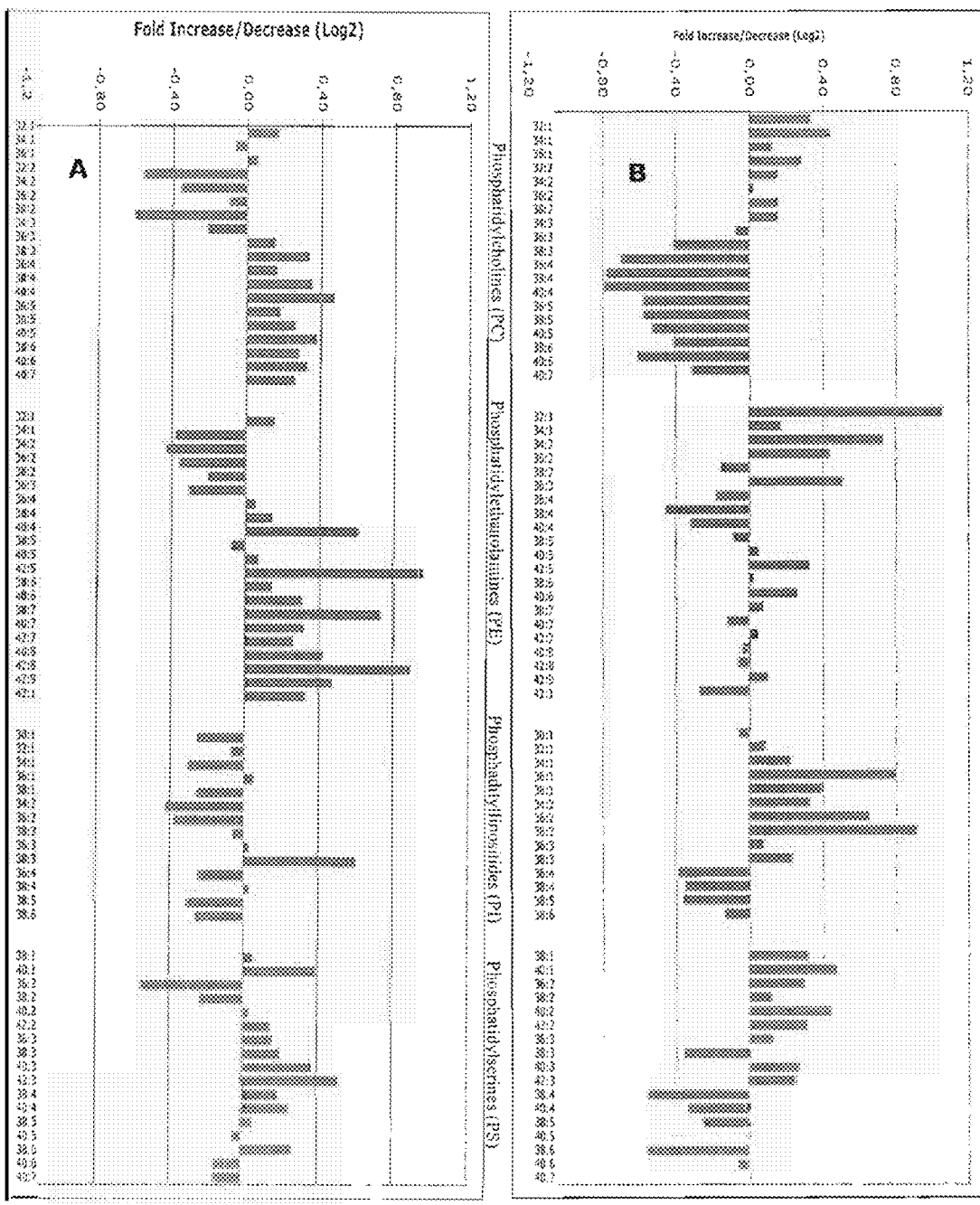
FIGS. 2A and 2B are graphs illustrating the average of relative changes in phospholipid species in prostate tumor versus normal prostate tissue from prostate cancer patients.

Cluster A (patients 3, 4, 5, 6, 7, 9, 10, 11 and 13), of which the average fold increase/decrease is represented in FIG. 2A, is characterized by a marked decrease in fully saturated PL species, an increase in species with one or two unsaturations (in both acyl chains together), and a decrease in PL species with more than 3 unsaturations. This pattern is most outspoken in the PC fraction and will be referred to as the lipogenic profile' as it can be largely explained by the lipogenic switch (Brusselmans, K., and Swinnen, J. V. (2009)). Apart from this lipogenic phenotype, also an elongation phenotype is evident for cluster A, in particular outspoken in the phosphatidylinositide and posphaditylserine phospholipid species. For the phosphatidylinositides a clear shift towards longer acyl chains can be observed for the lipid species having 2, 3 or 4 unsaturations, and in relation to the phosphatidylserines for the lipid species having 4, 5 and 6 unsaturations.

Based on these observations, Cluster A can be further divided in three subgroups (as represented in FIG. 1):

Cluster A1 (patients 9, 10, 11 and 13) contains tumors where the lipogenic profile is most outspoken and clearly visible in all PL families. In the PE fraction an additional shift towards shorter acyl chains was observed. PS and PI fractions showed an overall shift towards longer acyl chains.

Cluster A2 (patients 3, 4, 5 and 6) displays a high degree of similarity to cluster A1 in the PC species but the changes were less outspoken. The more unsaturated species in the other PL families also show a more limited decrease and even increase in the PE and PS fraction.

Cluster A3 (patient 7) shows a lipogenic profile in the PC species, but shows less outspoken changes in the other PL families.

Cluster B (patients 1, 2, 8 and 14) contains tumors which do not have an outspoken lipogenic profile, but a clearly distinguishable elongation phenotype (FIG. 2B) and can be further divided in two subgroups:

Cluster B1 (patients 2, 8 and 14) shows a pattern of PL changes associated with the lipogenic phenotype which are largely opposite to clusters A. However, all patients show an increase in acyl chain length in at least one of the phospholipid classes (FIG. 1). The elongation phenotype for patients 2 and 14 is most outspoken for the phosphatidylinositides, and for patient 8 it is most outspoken for the phosphatidylserines.

Cluster B2 (patient 1) is remarkable in the sense that it displays an increase in acyl chain elongation throughout all PL classes.

Patient 12 showed little change in PL profiles between tumor and normal tissue and cannot be classified within cluster A or B.

Example 2

Further Analysis of the Elongation Phenotype in Additional Prostate Tumor Patients To further analyze the observed elongation phenotype, prostate tumor tissue and matching normal tissue were collected from 21 prostate cancer patients who had undergone radical retropubic prostatectomy for localized prostatic carcinoma. All tumor samples were verified to consist for at least 75% of prostate adenocarcinoma by histological examination.

TABLE 2

Percentage of cancer tissue and Gleason grade of each tumor sample.

| Patient Number | Patient ID | Age at surgery | Gleason score | % of cancer in tumor sample |
|---|---|---|---|---|
| Patient 1 | P.8880 | 68 | 7 | 100 |
| Patient 2 | P.5735 | 66 | 7 | 95 |
| Patient 3 | P.4650 | 67 | 6 | 100 |

TABLE 2-continued

Percentage of cancer tissue and Gleason grade of each tumor sample.

| Patient Number | Patient ID | Age at surgery | Gleason score | % of cancer in tumor sample |
|---|---|---|---|---|
| Patient 4 | P.2125 | 75 | 6 | 90 |
| Patient 5 | P.5240 | 64 | 6 | 95 |
| Patient 6 | P.6445 | 69 | 6 | 95 |
| Patient 7 | P.0973 | 70 | 7 | 95 |
| Patient 8 | P.1204 | 69 | 4 | 80 |
| Patient 9 | P.1763 | 71 | 9 | 90 |
| Patient 10 | P.4567 | 70 | 6 | 85 |
| Patient 11 | P.9447 | 73 | 6 | 80 |
| Patient 12 | P.9483 | 63 | 6 | 85 |
| Patient 13 | P.4605 | 61 | 6 | 85 |
| Patient 14 | P.1326 | 69 | 7 | 80 |
| Patient 15 | P.6061 | 71 | 6 | 85 |
| Patient 16 | P.3720 | 65 | 7 | 80 |
| Patient 17 | P.9945 | 66 | 6 | 80 |
| Patient 18 | P.3113 | 62 | 8 | 100 |
| Patient 19 | P.6790 | 69 | 6 | 90 |
| Patient 20 | P.0204 | 61 | 6 | 75 |
| Patient 21 | P.3757 | 69 | 7 | 95 |

Lipids were extracted from both cancer and matched normal tissues and were analyzed by electrospray tandem mass spectrometry using a shotgun lipidomics approach. Detailed information of the used extraction and analysis methods can be found in example 1. Intact phospholipid species of four major classes; PC, PE, PS and PI were quantified in MRM mode. Profiles of normal tissues were all similar, although the relative contribution of individual species varied from sample to sample. To minimize confounding effects due to these inter-individual differences, the lipid profile of each cancer tissue was compared to its matched normal tissue. Remarkable changes in phospholipid profiles in cancer versus normal tissue were seen. To better visualize and interpret these changes we expressed differences in individual species as the ratio of the mole % of total measured lipid species in cancer versus matched normal tissue. This comparison revealed the extent of both common and distinct changes in cancerous versus normal tissues and among individual tumors.

Figures 3A, 3B:
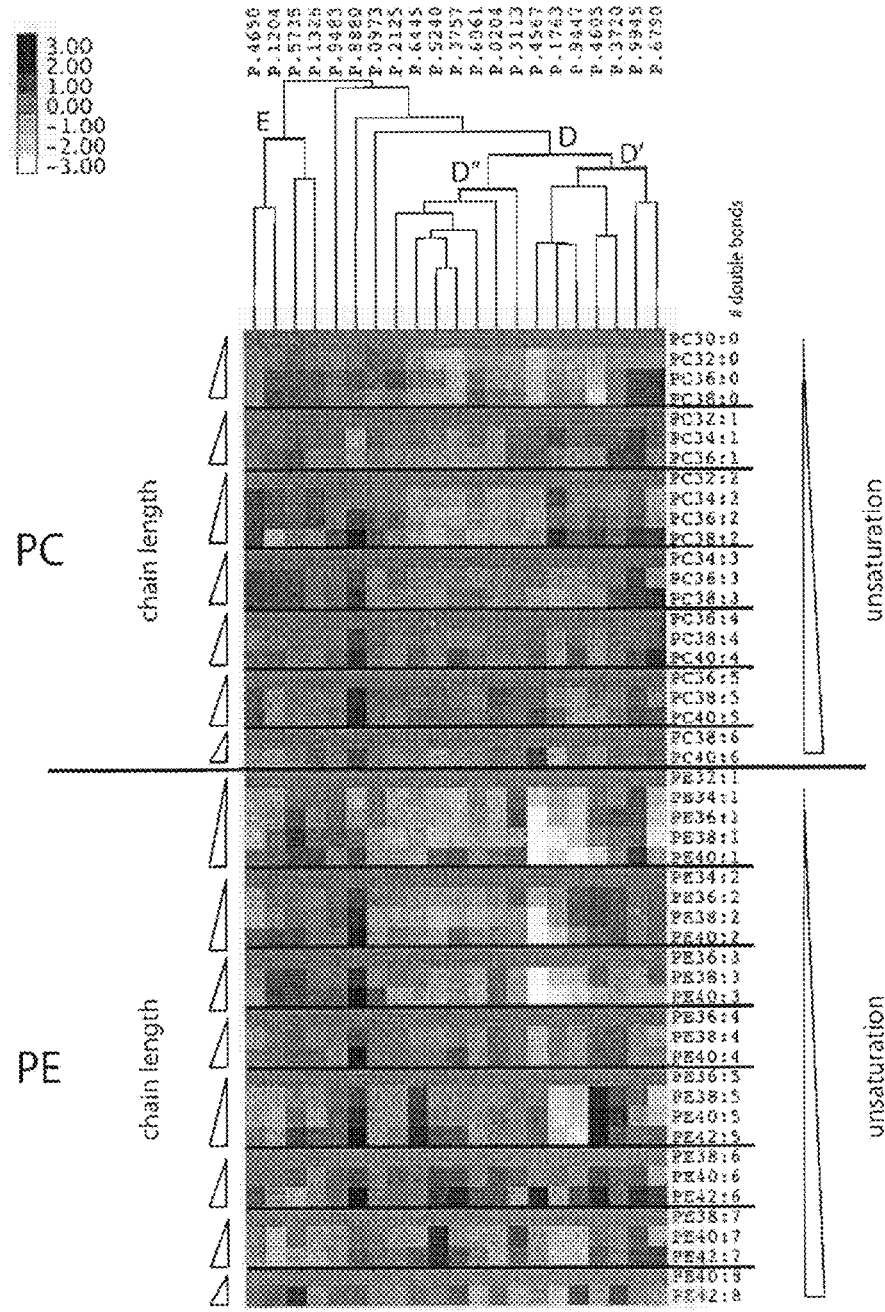
Figure 4:
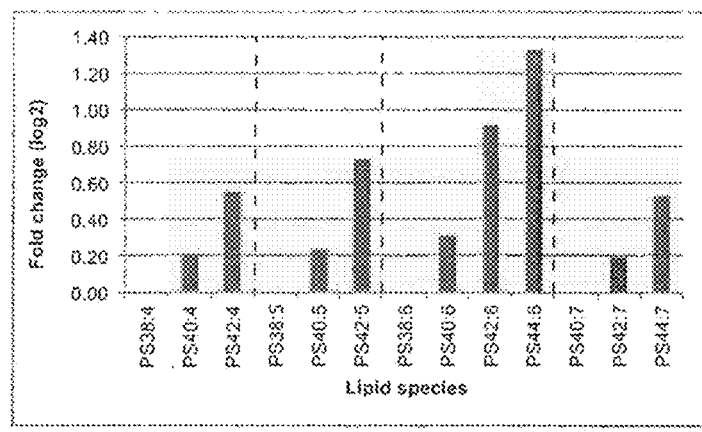
FIG. 4 is a graph illustrating elongation in PS species with 4-7 unsaturations.
Figure 5A:
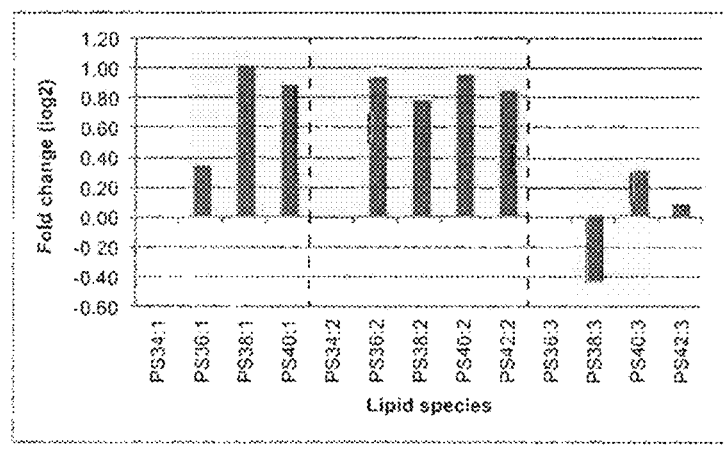
FIGS. 5A and 5B are graphs illustrating an elongation profile in PS species with 1-3 unsaturations.
Figure 5B:
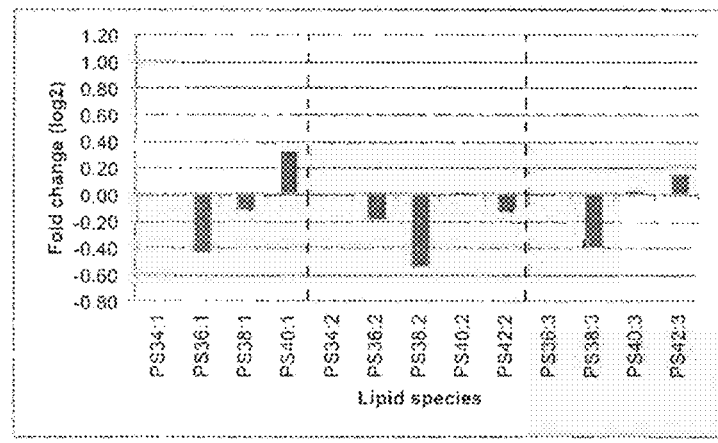
Figure 6:
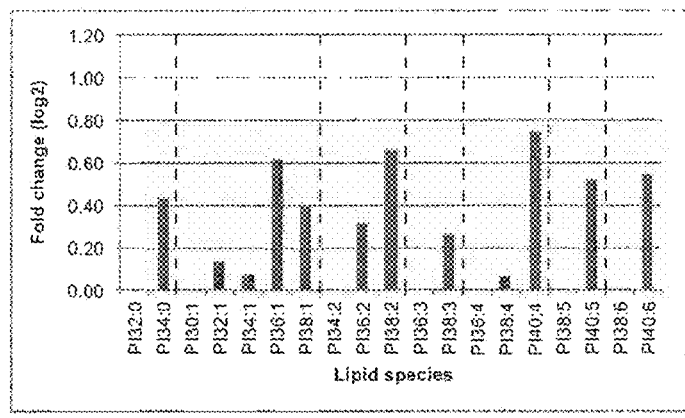
FIG. 6 is a graph illustrating overall elongation in PI species.
Figure 7A:
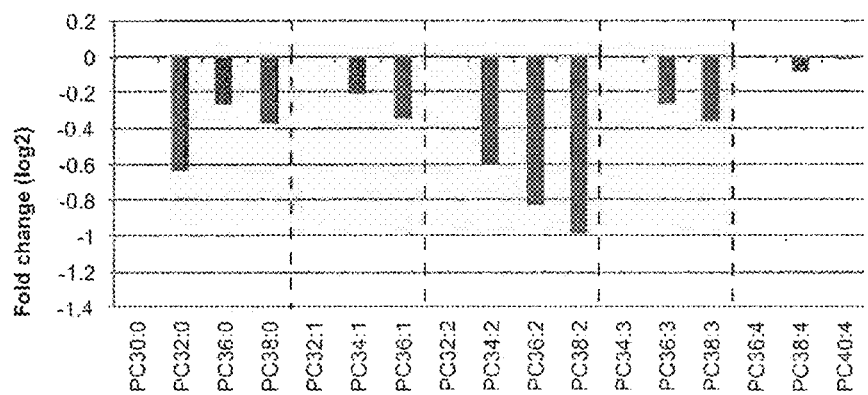
FIGS. 7A and 7B are graphs illustrating a decrease in elongation in PC and PE species with 1-4 unsaturations for patients in cluster D"
Figure 7B:
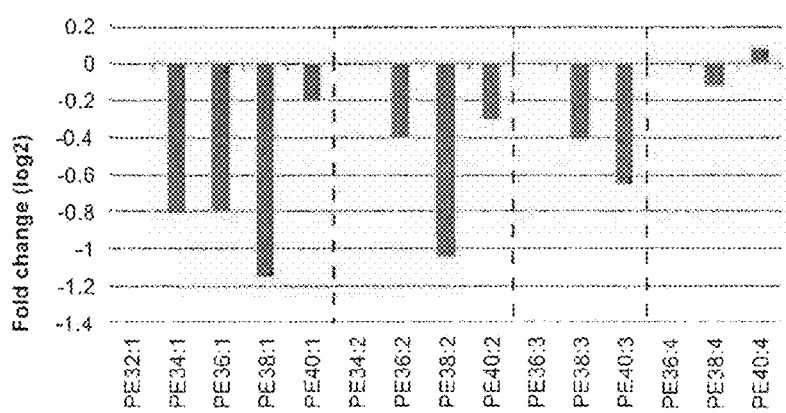
Figure 8A:
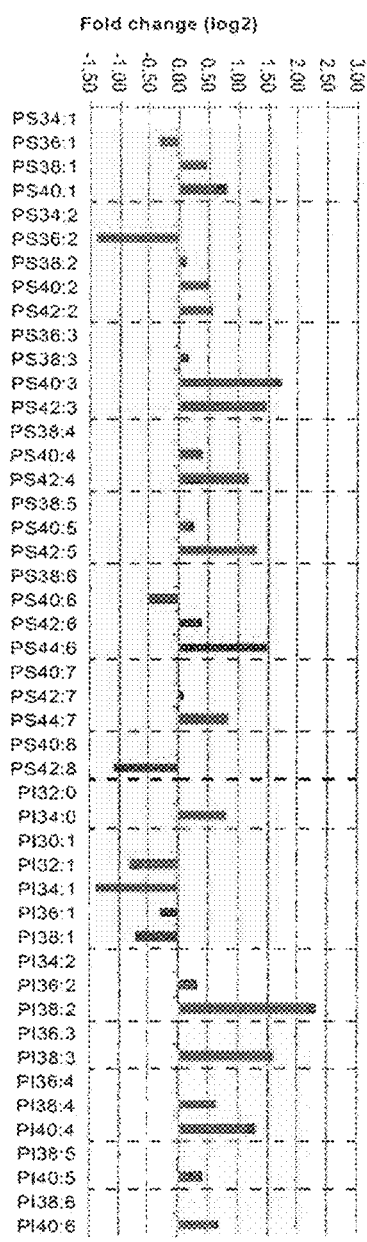
FIGS. 8A and 8B are graphs illustrating an increase in acyl chain length in all head group classes for patient P.8880.
Figure 8B:
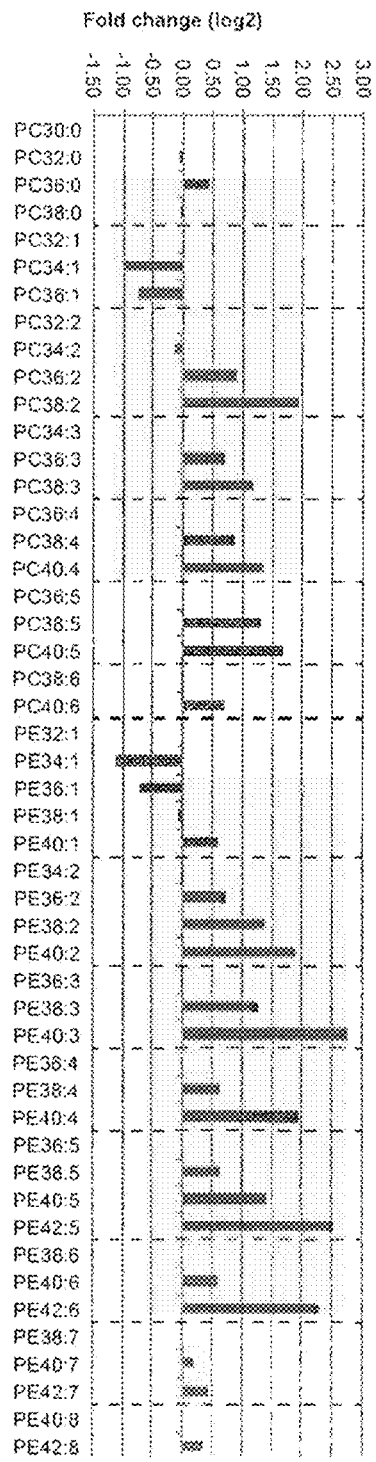

Recurrent changes included alterations in acyl chain length causing a checkered board-like appearance of the heatmap. To better reveal these changes we expressed in FIG. 3 the relative abundance of each phospholipid species in tumors and matching normal tissue relative to the shortest phospholipid species of each subclass of (un)saturation to optimally reveal changes in acyl chain length. This divided the patients in cluster D and E and revealed complex recurrent patterns of changes in acyl chain elongation. Most remarkable was a shift towards longer acyl chains in polyunsaturated PS (4 to 7 unsaturations in two acyl chains combined) (PS42:4 and PS40:4 versus PS38:4, $p<0.01$ and 0.05 respectively; PS42:5 versus PS38:5, $p<0.01$, PS44:6 and PS42:6 versus PS38:6, $p<0.01$; PS44:7 versus PS40:7, $p<0.01$) (FIG. 4). This shift was found in 17 out of 21 patients. More variable changes in acyl chain length were observed in PS with 1 to 3 unsaturations. These changes divided cluster D in 2 sub clusters, clusters D' and D". In cluster D' an additional relative increase in chain length for PS species with 1 to 3 unsaturations was seen (PS40:3 versus PS38:3, $p<0.05$; PS42:2, PS40:2, PS38:2 and PS36:2 versus PS34:2, $p<0.05$; PS40:1, PS38:1 and PS36:1 versus PS34:1, $p<0.05$) (FIG. 5a). These changes were not present in cluster D" (FIG. 5b). Cluster E did not show a clear pattern of changes in acyl chain length. An increase in acyl chain length was found also in PI species (PI38:2 and PI36:2 versus PI34:2, $p<0.01$; PI40:4 versus PI36:4, $p<0.0001$; PI40:5 versus PI 38:5, $p<0.0001$; PI40:6 versus PI38:6, $p<0.0001$) (FIG. 6). In a subset of patients (mainly in cluster D"), there was also a trend towards decreased chain length of PC and PE species with 1 to 4 unsaturations in tumors (FIG. 7). The most outspoken chain elongation phenotype was found in patient P.8880 who showed a nearly ubiquitous increase in acyl chain length in all head group classes (FIG. 8).

Example 3

Figures 9A, 9B:
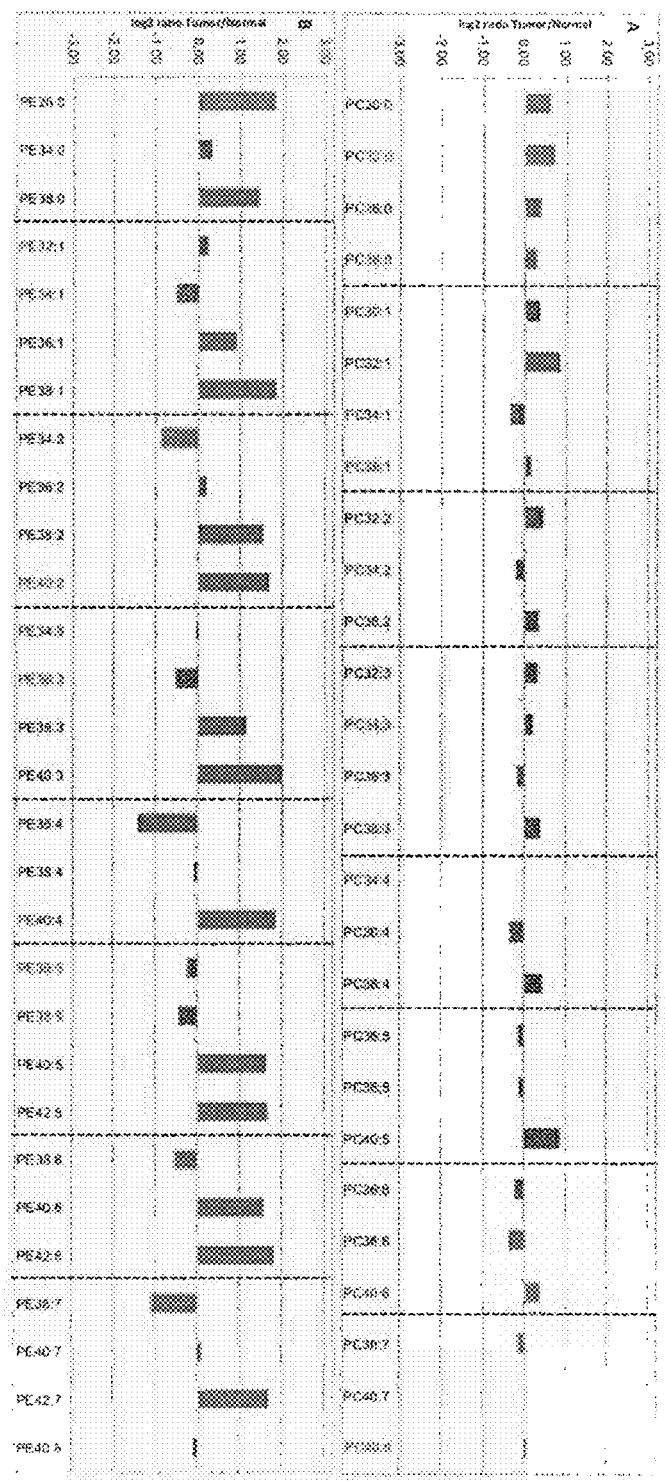
FIGS. 9A-9D are graphs illustrating changes in phospholipid profiles of ccRCC versus matched normal kidney cortex (n=20)
Figures 9C, 9D:
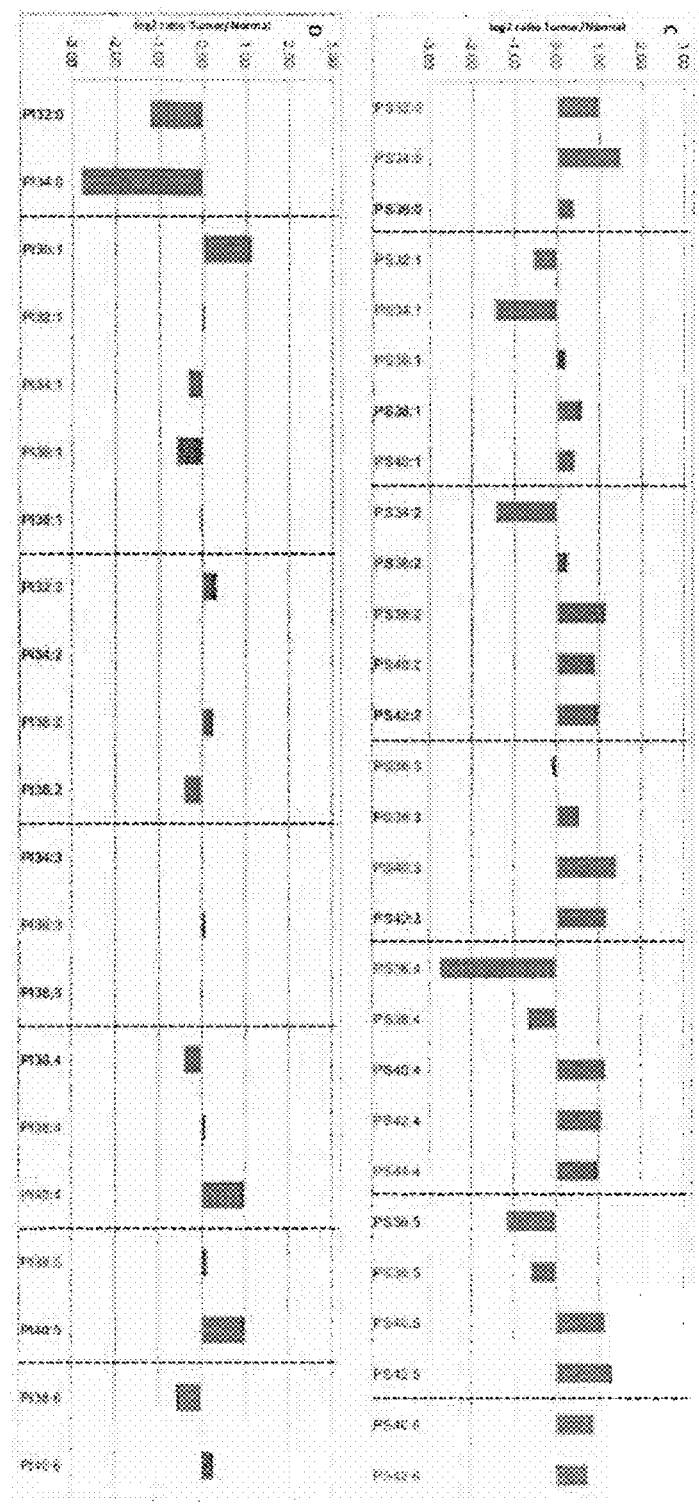

Phospholipid Profiling in an Extended Group of Clear Cell Renal Cell Carcinoma Patients Making Use of PC, PE, PS and PI Profiles Material and Methods
 Tissue Collection.
 Clear cell kidney tumor tissues (n=20) and matching normal cortex (n=20) samples were obtained from patients who had undergone an open radical nephrectomy for clear cell renal cell carcinoma (ccRCC). Samples were snap-frozen in liquid nitrogen and stored at −80° C. for lipid and protein extractions. Vital normal and tumor tissues were confirmed by HE-staining of a fresh frozen tissue section of the tissue samples.
 A detailed description of the methods used for lipid extraction and phospholipid analysis can be found in example 1. Only the phospholipid species with an intensity>5× the intensity of the blank are shown in the graphs.
Results
 Phospholipid analysis of ccRCC samples compared to matching normal tissues revealed marked differences in phospholipid profiles, particularly with respect to the acyl chain length. A marked elongation of acyl chains, particularly of very long chain polyunsaturated fatty acyl chains was in nearly all ccRCC samples. This elongation phenotype was most profound in the phosphatidylserine (PS) and phosphatidylethanolamine (PE) headgroup classes (FIG. 9).
 These data indicate that phospholipidome analysis of kidney samples has potential to detect the presence of clear cell renal cell carcinoma based on changes in acyl chain lengths.

Example 4

Evaluation of Phospholipidome Analysis of Exosome Fractions from Urine for Non-Invasive Detection/Diagnosis of Kidney Cancer A common disadvantage with currently available cancer diagnosis tools is the requirement of obtaining tumor samples. Therefore, it was an objective of this example to determine whether cancer diagnosis and the evolution of a tumor could be assessed via a less invasive method by determining the phospholipid profile of exosomes obtained from urine or blood serum samples.
Methods
 Urine and blood serum samples were collected from kidney cancer patients before and after surgical tumor resection. Exosome fractions were prepared by differential ultracentrifugation. Presence and purity of exosomes was monitored by transmission electronmicroscopy and western blot analysis with antibodies against flotillin and transferrin receptor (de Gassart et al., 2003). Lipids were extracted from exosomes and from primary tumor tissues using an in-house modified Bligh-Dyer protocol after addition of appropriate lipid standards and antioxidants. Lipid species were analyzed by electrospray ionization tandem mass spectrometry (ESI- MS/MS) on a hybrid triple quadrupole linear ion trap (4000 QTRAP) system equipped with an Advion TriVersa Nano-Mate nozzle chip-based infusion system for automated sample injection from 96-well plates. Samples were analyzed in MRM mode using an in-house developed protocol for detection and quantification of all major phospholipid species.

Results

Figure 10:
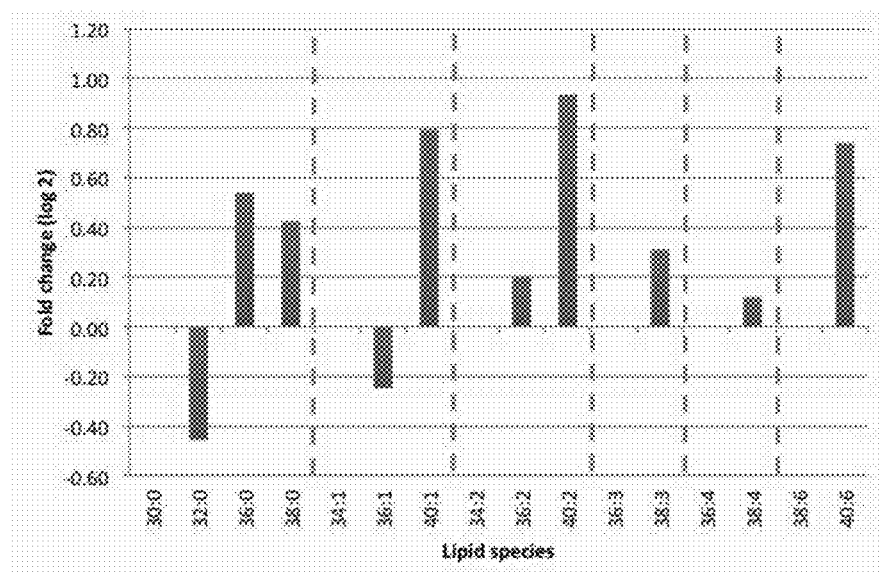
FIG. 10 is a graph illustrating changes in phospholipid acyl chain length in exosomes isolated from pre-operative urine samples versus post-operative samples from kidney cancer patients.

Phospholipid analysis of exosomes from urine from kidney cancer patients before surgical resection (presence of tumor) and after surgical resection (absence of tumor) reveal significant changes, including a marked shift towards longer acyl chain species, in phospholipid profiles of exosomes from pre-operative (presence of tumor) versus postoperative (absence of tumor) urine. These changes largely correlate with those of the primary tumor and indicate that the presence of a tumor can be detected in urine samples only based on phospholipid profiles from urine exosomes (FIG. 10). Exosomes are membrane-based microvesicles that are released by cells into body fluids, including urine (Al-Nedawi et al., 2009). Numerous reports indicate that particularly cancer cells are active in producing high amounts of exosomes (Al-Nedawi et al., 2009; Aethlon Medical, 2010). Concordantly, exosome levels in cancer patients often are up to 10-fold higher than healthy control. Moreover, as cancer is often multifocal, data based on one biopsy may not reflect the situation of the entire tumor, and therefore may not accurately predict the outcome of the disease. In contrast, circulating exosomes reflect the whole tumor and are readily accessible and amenable for less invasive biomarker analysis. Here, we demonstrate that phospholipidomics of exosome fractions of urine samples has the potential to detect/diagnose the presence of kidney cancer. These data provide the proof-of-principle for a non-invasive screening test for kidney cancer detection/diagnosis based on changes in phospholipid profiles of exosome fractions from urine samples.

Example 5

Evaluation of Phospholipidome Analysis for Assessment of Treatment Response

Methods

GIST T1 cells were treated with 0.1 micromolar imatinib. Lipids were extracted after 72 hours using an in-house modified Bligh-Dyer protocol after addition of appropriate lipid standards and antioxidants. Lipid species were analyzed by electrospray ionization tandem mass spectrometry (ESI-MS/MS) on a hybrid triple quadrupole linear ion trap (4000 QTRAP) system equipped with an Advion TriVersa Nano-Mate nozzle chip-based infusion system for automated sample injection from 96-well plates. Samples were analyzed in MRM mode using an in-house developed protocol for detection and quantification of all major phospholipid species.

Results

Figures 11A, 11B:
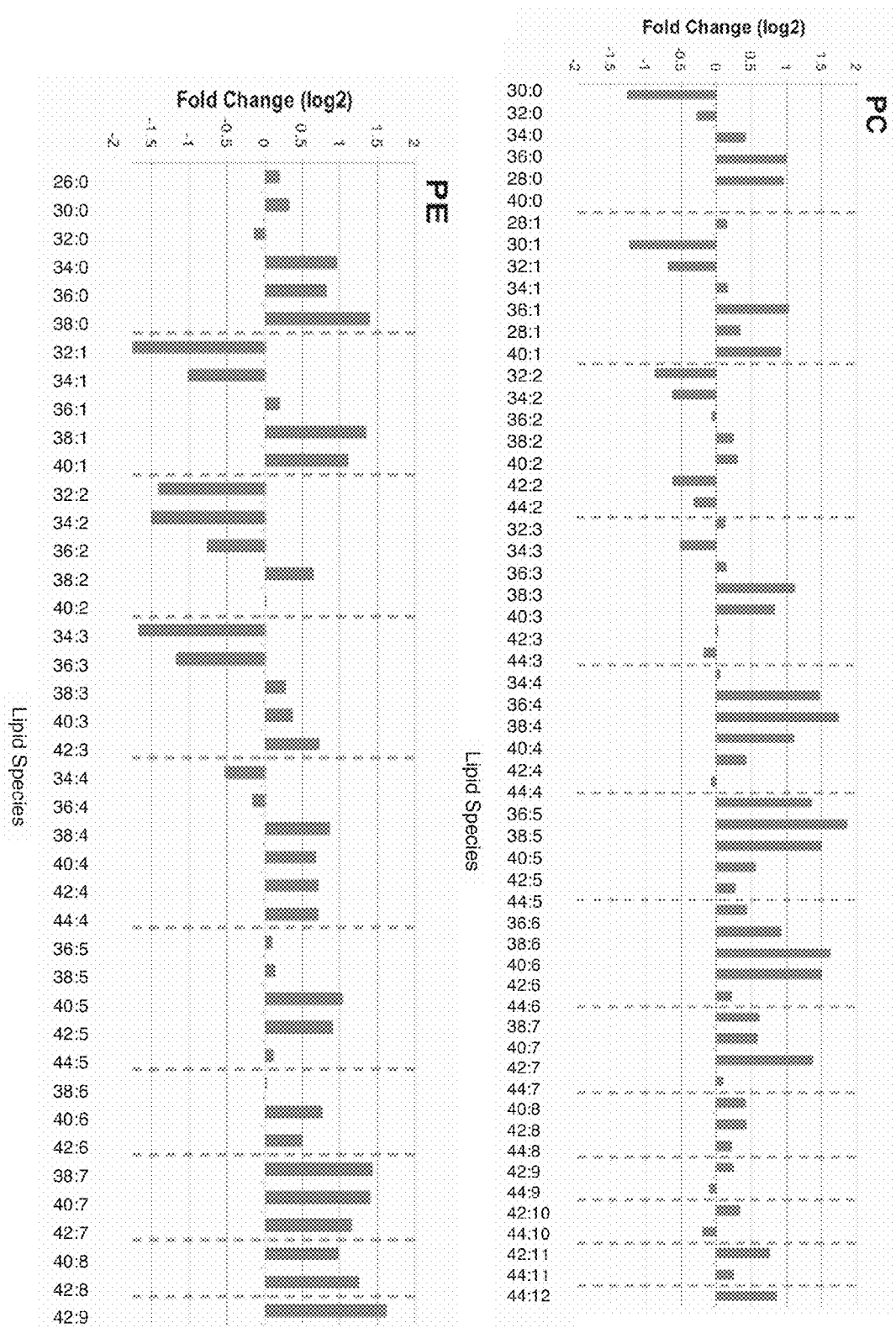
FIGS. 11A-11D are graphs illustrating changes in phospholipid acyl chain length in GIST T1 cells treated for 72 hours with 0.1 micromolar imatinib.
Figure 11C:
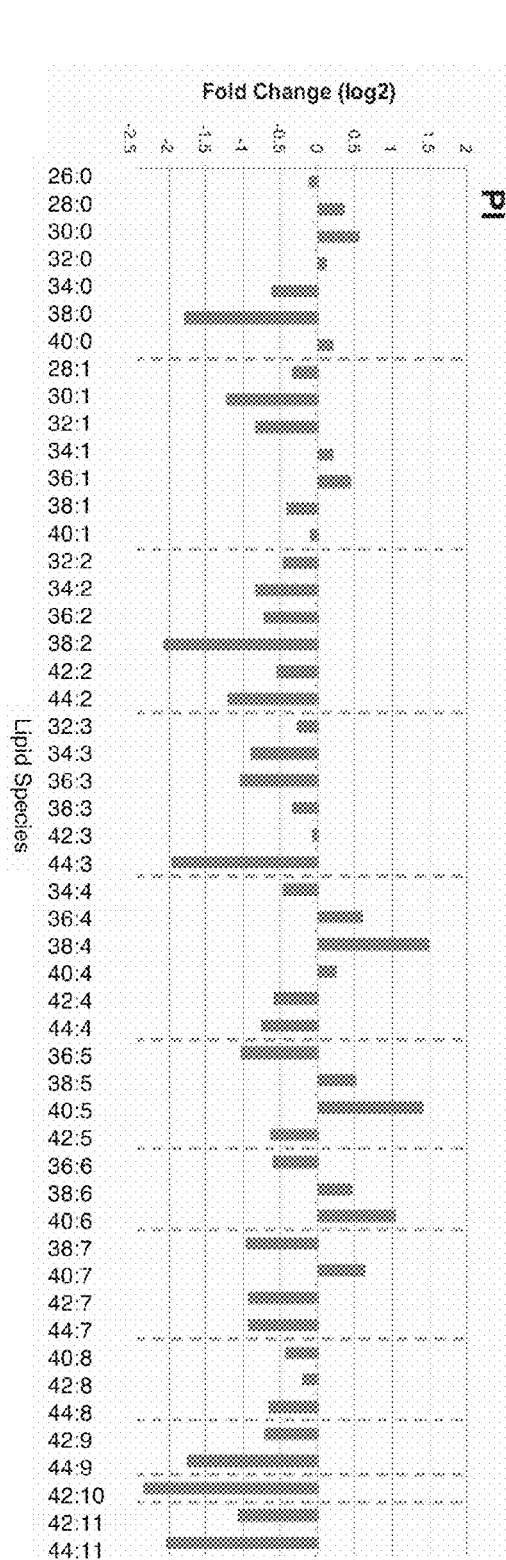
Figure 11D:
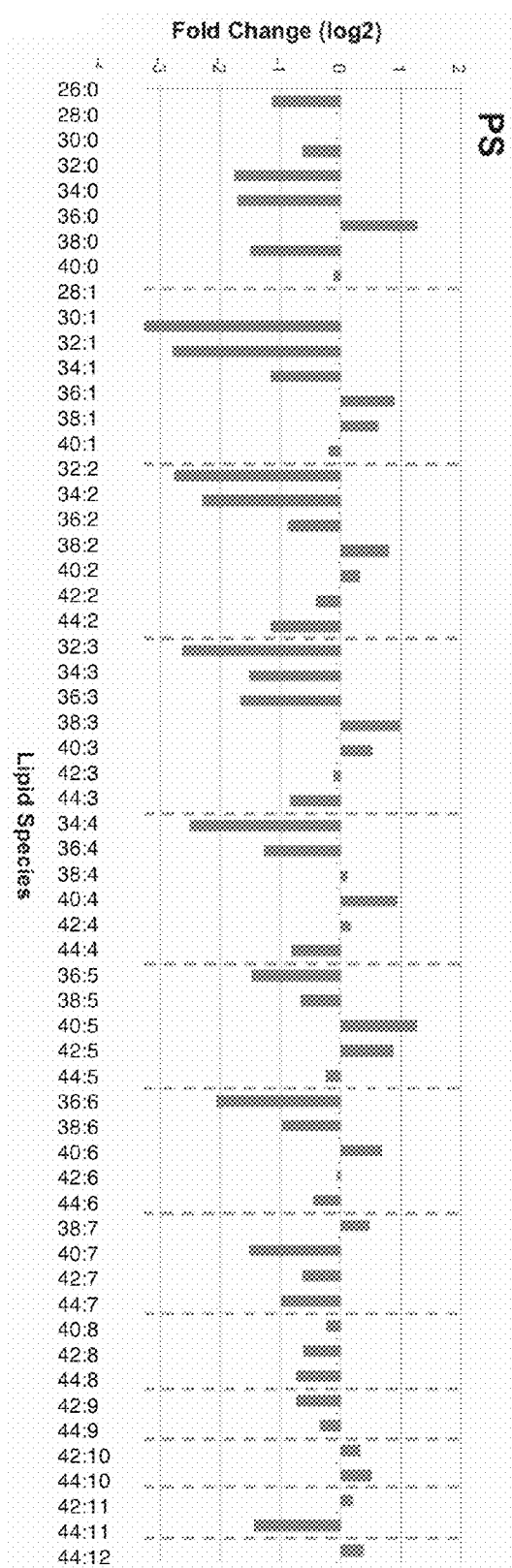

Phospholipid analysis of imatinib-responsive GIST T1 cells reveals major changes in phospholipid profiles after imatinib treatment. Characteristic changes include a moderate elongation of acyl chains resulting in a shift of phospholipid species within each subclass of species with an equal number of unsaturations from the shortest towards longer ones, often also accompanied by a relative decrease of the longest species, particularly in PC, PS and some PI species (see FIG. 11). These data indicate that responsiveness to imatinib is accompanied by major changes in phospholipid profiles. They also provide proof-of-principle that phospholipid profiling may be used to follow-up treatment responsiveness of tumors.

Example 6

Inhibition of Fatty Acyl Chain Elongation Attenuates Cancer Cell Proliferation

Materials & Methods

Cell Culture

Renal cancer cell lines RCC4 VHL (Von Hippel Lindau) positive and negative were cultured in advanced DMEM supplemented with 10% fetal bovine serum, 1% PSG and 0.5 mg/ml G418. Cells were grown at 37° C. in a humidified 5% $CO_2$ incubator. The day after seeding, cells were treated with 100 nm soraphen or vehicle (control) for 72 h.

Results

Figures 12A, 12B:
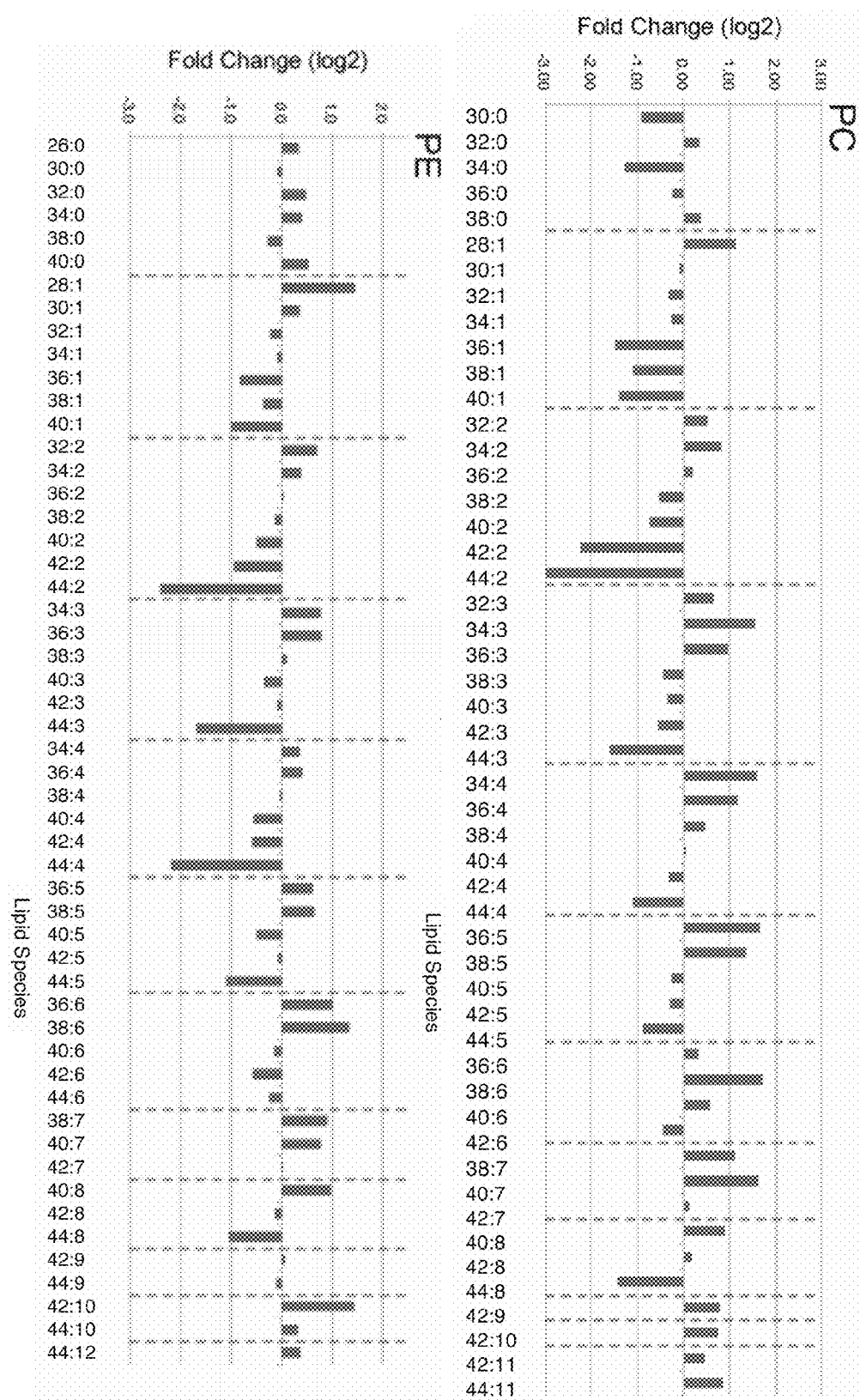
FIGS. 12A-12D are graphs illustrating changes in phospholipid acyl chain composition in soraphen treated MDA-MB-231 breast adenocarcinoma cells versus control (vehicle treated) cells.
Figure 12C:
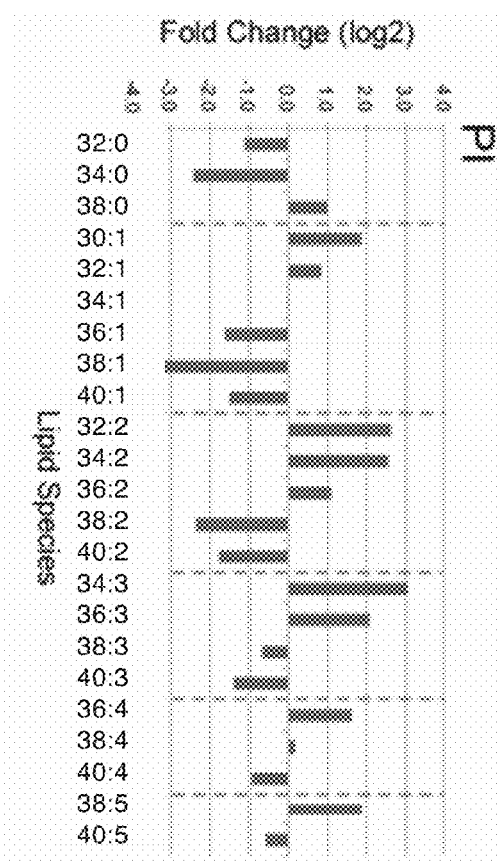
Figure 12D:
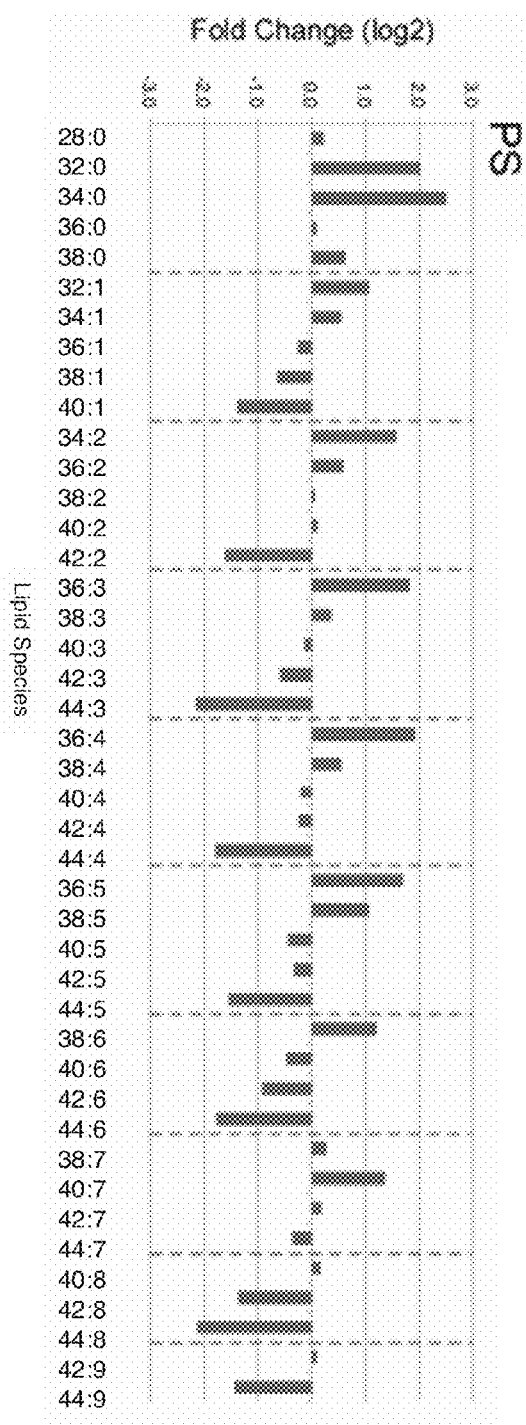

To assess the impact of fatty acyl chain elongation and of chemical inhibitors of this process, the human renal cell carcinoma cell line RCC4 was treated with soraphen. To demonstrate that soraphen selectively inhibits acyl chain elongation in this model, lipids were extracted from both soraphen and vehicle treated cells and were analyzed by tandem mass spectrometry. The lipid profiles reveal a marked shift from longer to shorter lipid species when cells are treated with soraphen, which is indicative of inhibition of acyl chain elongation (FIG. 12). Conversely, these data reveal that acyl chain elongation and the resulting increase in acyl chain length of phospholipids stimulates tumor growth and contributes to the progression of tumors. These data also indicate that inhibitors of the elongation process may be used to slow down tumor growth and may have potential for antineoplastic treatment.

Example 7

Inhibition of Fatty Acyl Chain Elongation Decreases Cancer Cell Invasiveness

Materials & Methods

Cell Culture

Human breast adenocarcinoma cells MDA-MB-231 (obtained from the American Type Culture Collection) were cultured in DMEM-F12 supplemented with 10% fetal bovine serum and were grown at 37° C. in a humidified 5% $CO_2$ incubator. The day after seeding, cells were treated with 100 nm soraphen or vehicle (control) for 72 h.

Assessment of Gelatinolytic Activity by Confocal Microscopy

MDA-MB-231 cells were treated with soraphen or vehicle for 72 h. Treated cells were trypsinized and seeded on top of Matrigel® matrix containing 25 µg/ml of DQ-Gelatin® (Invitrogen) in a 8-well Lab-Tek™ II Chamber Slide™. Cells were counted and seeded at a density of 10.000 cells per well. After 24 h cells were fixed for 10 min in 3.7% formaldehyde in phosphate-buffered saline. Confocal microscopy was performed with an Olympus Fluoview FV1000 instrument. The samples were excited at 488 nm, and emission light was recorded at 515 nm. Fluorescence intensity was quantified as the mean gray value in ImageJ software version 1.45e (National Institutes of Health, Bethesda, Md., USA).

Results

Inhibition of Fatty Acid Elongation Decreases Cancer Cell Invasiveness

Figures 13A, 13B:
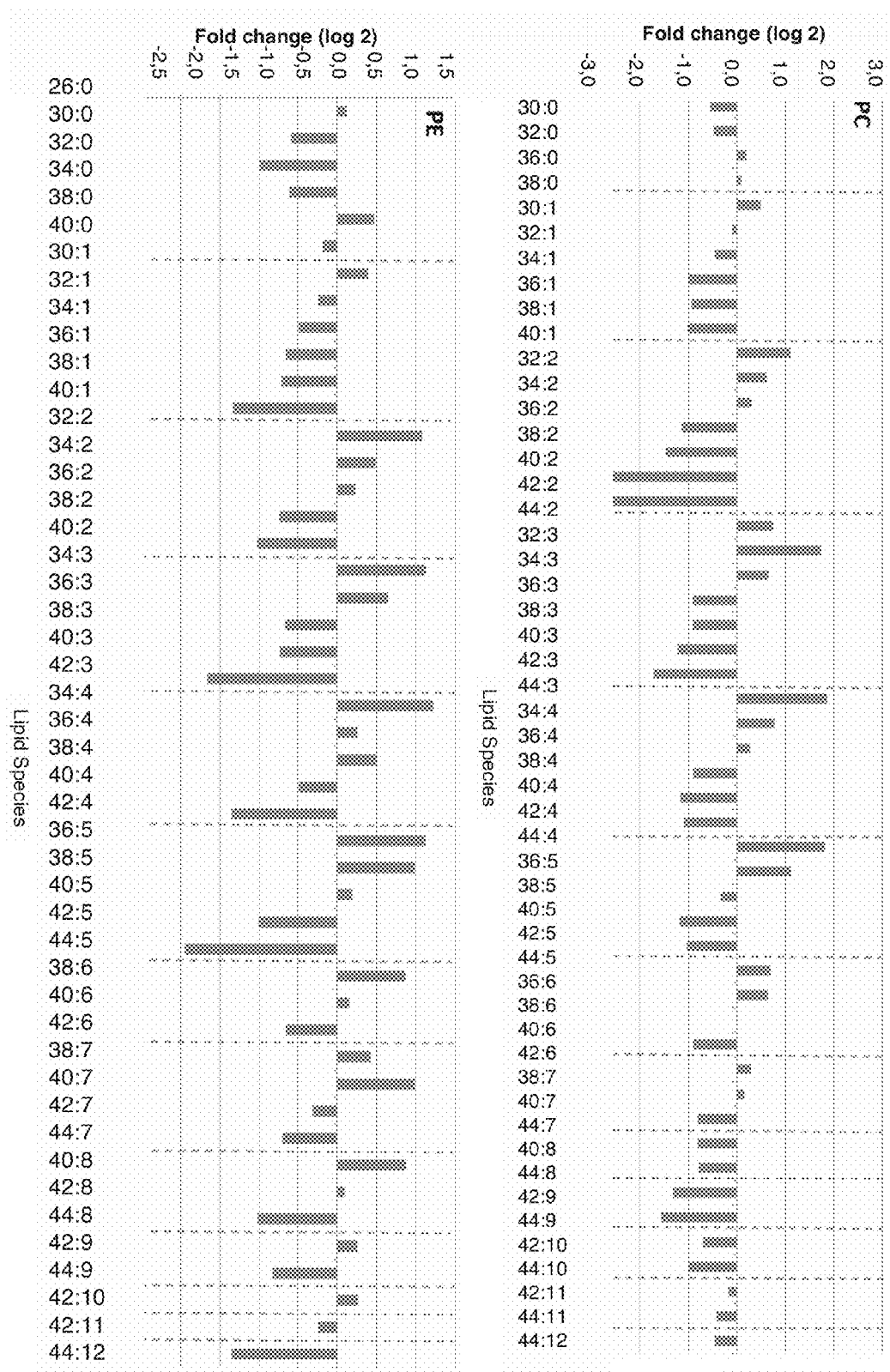
FIGS. 13A-13D are graphs illustrating changes in phospholipid acyl chain composition in RCC4 cells treated with soraphen versus control (vehicle treated) cells. Lipid profiling was performed in three pairs of samples.
Figure 13C:
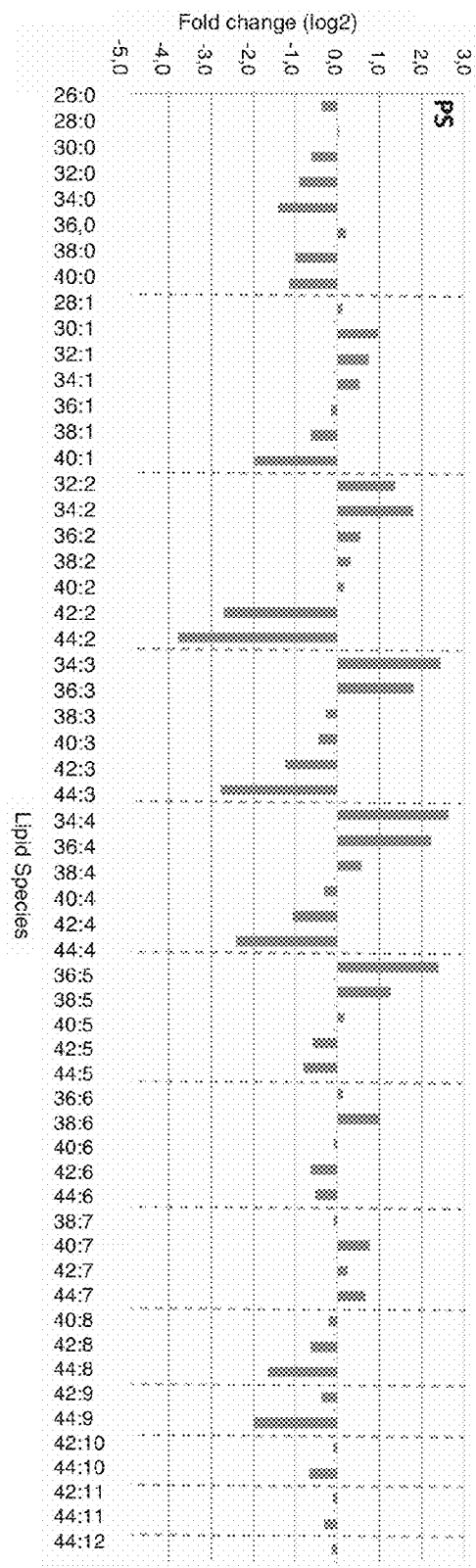
Figure 13D:
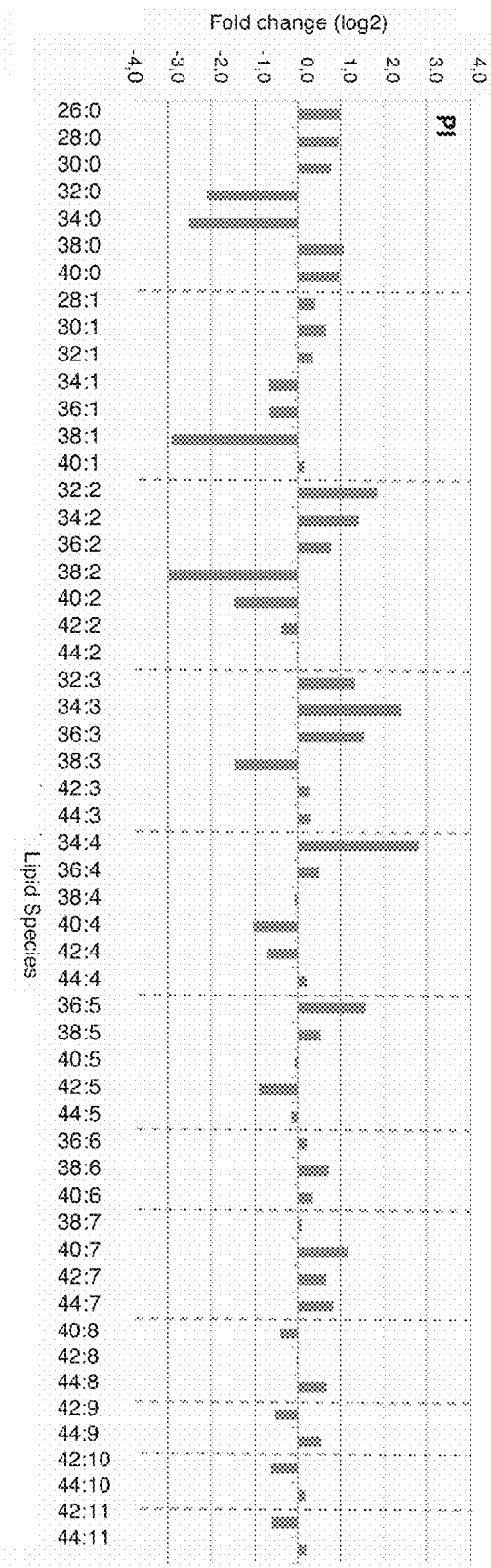

Lipids were extracted from both soraphen and vehicle treated cells and were analyzed by tandem mass spectrometry. The lipid profiles reveal a marked shift from longer to shorter lipid species when cells are treated with soraphen (FIG. 13).

Example 8

Extraction Method for Phospholipids Based on HLB SPE

Materials & Methods
SPE cartridge: Supel-Select HLB SPE tube (30 mg/1 mL)
SPE Manifold Test Tubes: Test Tubes, 10×75 mm
Anti-oxidant (BHT): 1 mM solution in ethanol
Sample Diluent: 10:90/Methonal: water (MS grade)
Conditioning solvent A: water (MS grade)
Conditioning solvent B: Methanol (MS grade)
Wash solvent A: water (MS grade)
Wash solvent B: 10:90/Methanol: water (MS grade)
Elution solvent: 75:25/Methanol: Acetonitrile (MS grade)
Sample Preparation for SPE:
   Take 200 µl of sample (cell or tissue suspension) in test tube.
   Add 800 µl of cold sample diluent and 5 µl of anti-oxidant (BHT)
   Vortex for 2 min.
   Centrifuge at 1000 rpm
   Use the supernatant sample for SPE
SPE Procedure:
   1. Place new SPE cartridge on SPE Vacuum Manifold for each sample
   2. Place test tube's on test tube rack inside SPE Vacuum Manifold
   3. Pass the 1.5 ml of conditioning solvent A through the SPE.
   4. Pass the 1.5 ml of conditioning solvent B through the SPE.
   5. Pass the sample (1 ml) through SPE cartridge
   6. Replace test tubes in side SPE Vacuum Manifold
   7. Wash the cartridge with 1 ml of wash solvent A.
   8. Wash the cartridge with 1 ml of wash solvent B.
   9. Replace test tubes in side SPE Vacuum Manifold
   10. Elute the lipids with 1 ml of elution solvent
   11. Dry the test tube in speedvac
   12. Pass argon gas into the test tube
   13. Store at −20° C. for MS based Lipidomics analysis.
Note: All the Solvents and Sample should be at 0 to 5° C. During the Extraction

REFERENCES

Al-Nedawi K., Meehan G., Rak J., *Microvesicles: messengers and mediators of tumor progression,* 2009 Cell Cycle July 1; 8(13) 2014-2018
Brugger, B., G. Erben, R. Sandhoff, F. T. Wieland, and W. D. Lehmann, *Quantitative analysis of biological membrane lipids at the low picomole level by nanoelectrospray ionization tandem mass spectrometry.* Proc Natl Acad Sci USA, 1997. 94(6): p. 2339-44
Brusselmans, K., and Swinnen, J. V. (2009) *The lipogenic switch in Cancer.* Mitochondria and Cancer K K Singh and L. C. Costello, Eds, Springer, New York, USA pp. 39-59
Crowe, F., Allen, N., Appleby, P., et al. (2008) *Fatty acid composition of plasma phospholipids and risk of prostate cancer in a case-control analysis nested within the European Prospective Investigation into Cancer and Nutrition.* Am. J. Clin. Nutrition 88: 1353-1363
de Gassart A., Geminart C., Fevrier B., Raposo G., Vidal M., *Lipid raft associated protein sorting in exosomes,* Blood, 2003 Dec. 15; 102(13)4336-44
Eisen, M. B., P. T. Spellman, P. O. Brown, and D. Botstein, *Cluster analysis and display of genome-wide expression patterns.* Proc Natl Acad Sci USA, 1998. 95(25): p. 14863-8
Gennadi V. Glinsky, Anna B. Glinskii, Andrew J. Stephenson, Robert M. Hoffman, William L. Gerald. *Gene expression profiling predicts clinical outcome of prostate cancer.* Journal Clinical investigation 113: 913-923 (2004)
Gering J. P., Quaroni L., Chumanov G., *Immobilization of antibodies on glass surfaces through sugar residues.* J Colloid Interface Sci. 2002 Aug. 1; 252(1): 50-6.
Godley, P., Campbell, M., Gallagher, P., et al. (1996). *Biomarkers of Essential Fatty Acid Consumption and Risk of Prostatic Carcinoma.* Cancer Epidemiology, Biomarkers & Prevention 5, 889-895
Harvei S., Bjerve K. S., Tretli S. Jellum E., Robsahm T. E., Vatten L., *Prediagnostic level of fatty acids in serum phospholipids: omega-3 and omega-6 fatty acids and the risk of prostate cancer.* Int. J. Cancer. 1997 (71), 545-551
Johnson R. J., McCoy J. G., Bingman C. A., Philips G. N., Raines R. T., *Inhibition of human pancreatic ribonuclease by the human ribonuclease inhibitor protein.* 2007 Journal of Molecular Biology 368 (2): 434-449
Kuemmerle N B, Rysman E, Lombardo P S, Flanagan A J, Lipe B C, Wells W A, Pettus J R, Froehlich H M, Memoli V A, Morganelli P M, Swinnen J V, Timmerman L A, Chaychi L, Fricano C J, Eisenberg B L, Coleman W B, Kinlaw W B. *Lipoprotein lipase links dietary fat to solid tumor cell proliferation.* Mol Cancer Ther. 2011 March; 10(3):427-36
Mannelli I., Minunni M., Tombelli S., Wang R., Spiriti M., Mascini M., *Direct immobilisation of DNA probes for the development of affinity biosensors.* Bioelectrochemistry Volume 66, Issues 1-2, April 2005, Pages 111-115
Männistö S., Pietinen P., Virtanen M. J., Salminen I., Albanes D., Giovannucci E., Virtamo J., *Fatty acids and risk of prostate cancer in a nested case-control study in male smokers.* Cancer Epidemiology, Biomarkers & Prevention, 2003 (12) 1422-1428
Manz, A. and Becker. H. (Eds.), *Microsystem Technology in Chemistry and Life Sciences,* Springer-Verlag Berlin Heidelberg New York, ISBN 3-540-65555-7
Marguet D, Lenne P F, Rigneault H, He H T (2006) *Dynamics in the plasma membrane: how to combine fluidity and order.* EMBO J 25: 3446-3457
Milne et al [Milne, S., P. Ivanova, J. Forrester, and H. Alex Brown, *Lipidomics: an analysis of cellular lipids by ESI-MS.* Methods, 2006. 39(2): p. 92-103.]
Saldanha, A. J., *Java Treeview—extensible visualization of microarray data.* Bioinformatics, 2004. 20(17): p. 3246-8
Swinnen, J. V., Brusselmans, K., and Verhoeven, G. (2006). *Increased lipogenesis in cancer cells: new players, novel targets.* Curr Opin Clin Nutr Metab Care 9, 358-365
Tamura K, Makino A, Hullin-Matsuda F, Kobayashi T, Furihata M, Chung S, Ashida S, Miki T, Fujioka T, Shuin T, Nakamura Y, Nakagawa H. *Novel lipogenic enzyme ELOVL7 is involved in prostate cancer growth through saturated long-chain fatty acid metabolism.* Cancer Res. 2009 Oct. 15; 69(20):8133-40.)
Valadi H, Ekstrom K, Bossios A, Sjostrand M, Lee J J, Lotvall J O. *Exosome-mediated transfer of mRNAs and microRNAs is a novel mechanism of genetic exchange between cells.* Nat Cell Biol 2007; 9:654-659 van't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R, Friend S H. *Gene expression profiling predicts clinical outcome of breast cancer* Nature. 2002 Jan. 31; 415(6871):530-6.

Zhang Y, Liu D, Chen X, Li J, Li L, Bian Z, Sun F, Lu J, Yin Y, Cai X, Sun Q, Wang K, Ba Y, Wang Q, Wang D, Yang J, Liu P, Xu T, Yan Q, Zhang J, Zen K, Zhang C Y. *Secreted monocytic miR-150 enhances targeted endothelial cell migration*. Mol Cell 2010; 39:133-144

The invention claimed is:

1. An in vitro method for subtyping a tumor in a human subject, said method comprising:
   obtaining a tumor sample from said subject;
   isolating intact phospholipid species in at least one head group class from said tumor sample;
   determining a relative expression level of said intact phospholipid species in said at least one head group class in said tumor sample versus a normal sample using mass spectrometry (MS); and
   comparing changes in the relative expression level of phospholipid species having a same saturation level but different acyl chain lengths within said at least one head group class, to subtype said tumor;
   wherein a relative increase in longer chain phospholipid species compared to shorter chain phospholipid species within a head group class having the same saturation level is indicative of a tumor having an aggressive elongation phenotype, and
   wherein the shorter chain phospholipid species are phospholipid species with the same head group and equal number of unsaturations but with shorter than average (combined) acyl chain lengths selected from the group consisting of PC30:0, PC32:1, PC34:1, PC32:2, PC34:2, PC34:3, PC36:4, PC36:5, PC38:6; PE32:1, PE34:1, PE34:2, PE36:3, PE36:4, PE36:5, PE38:6, PE38:7, PE40:8, PS34:1, PS36:1, PS34:2, PS36:3, PS36:4, PS38:4, PS38:5, PS38:6 PS40:7; PI32:0, PI34:0, PI30:1, PI34:2, PI36:3, PI36:4, PI38:5 and PI38:6.

2. The in vitro method according to claim 1 further comprising determining the expression level of at least one mono-unsaturated phospholipid species and at least one poly-unsaturated phospholipid species, wherein an increase in relative expression level of said at least one mono-unsaturated phospholipid species and a decrease in relative expression level of said at least one poly-unsaturated phospholipid species is indicative for a more aggressive lipogenic phenotype.

3. The in vitro method according to claim 1, wherein the phospholipid species are selected from the group consisting of glycerophospholipid, phosphatidic acid, phosphatidylethanolamines, phosphatidylcholines, phosphatidylserines, sphingolipids, cardiolipins and phosphatidylinositides.

4. The in vitro method according to claim 3, wherein the phospholipid species within at least one head group class are selected from the group consisting of phosphatidylcholines, phosphadidylethanolamines, phosphatidylserines and phosphatidylinositides.

5. The in vitro method according to claim 2, wherein the mono-unsaturated phospholipid species are phosphatidylcholines (PC) with one or two mono-unsaturated fatty acyl chains selected from the group consisting of a PC having a combined acyl chain length of 28 and 1 unsaturation (PC28:1), PC30:1, PC30:2, PC32:1, PC32:2, PC34:1, PC34:2, PC36:1, PC36:2, PC38:1, PC38:2, PC40:1 and PC40:2.

6. The in vitro method according to claim 2, wherein the poly-unsaturated phospholipids are poly-unsaturated phosphatidylcholines (PC), selected from the group consisting of PC32:3, PC34:2, PC34:3, PC34:4, PC36:2, PC36:3, PC36:4, PC36:5, PC36:6, PC38:2, PC38:3, PC38:4, PC38:5, PC38:6, PC38:7, PC40:2, PC40:3, PC40:4, PC40:5, PC40:6, PC40:7, PC40:8, PC42:2, PC42:3, PC424, PC42:5, PC42:6, PC42:7, PC42:8, PC42:9, PC42:10, PC42:11, PC44:2, PC44:3, PC44:4, PC44:5, PC44:6, PC44:7, PC44:8, PC44:9, PC44:10, PC44:11 and PC44:12.

7. The in vitro method according to claim 2, wherein the mono-unsaturated phospholipids are the mono-unsaturated phosphatidylcholines (PC) PC34:1; and wherein the poly-unsaturated phospholipids are the poly-unsaturated phosphatidylcholines (PC) PC36:4 and/or PC38:4.

8. The method according to claim 1, wherein the shorter chain phospholipid species are selected from the group consisting of PC34:1, PC34:2, PE34:1, PE34:2, PE 36:4, PS34:1, PS36:1 PS34:2, PS36:4, PS38:4, PI32:0, PI34:0 and PI36:4.

9. The method according to claim 1 further comprising measuring the relative expression or phosphorylation/activation of one or more other biomarkers for an aggressive lipogenic phenotype in said tumor sample versus said normal sample; wherein an increase in relative expression of said one or more other biomarkers is indicative for a more aggressive lipogenic phenotype.

10. The method according to claim 9, wherein the one or more other biomarkers for an aggressive lipogenic phenotype are selected from the group consisting of fatty acid synthase (FASN), acetyl CoA carboxylase alpha (ACCA), and ATP citrate lyase (ACLY).

11. The method according to claim 1, wherein the expression level of phospholipids is determined via the analysis of phospholipids by tandem electrospray ionization mass spectrometry (ESI-MS/MS).

12. The method according to claim 1, wherein the lipid extraction method comprises hydrophilic lipophilic balanced Solid-Phase Extraction (HLB SPE).

13. The method according to claim 1, wherein the tumor sample is selected from the group consisting of prostate cancer; renal cancer, breast cancer; lung cancer; colon cancer; stomach cancer; ovarian cancer; endometrium cancer; liver cancer; oesophagus cancer; bladder cancer; oral cavity cancer; thyroid cancer; pancreas cancer; retina cancer and skin cancer.

14. The in vitro method according to claim 11 including using a kit comprising reagents for tandem electrospray ionization mass spectrometry (ESI-MS/MS) for analyzing the phospholipids isolated from the sample.

15. The in vitro method according to claim 14, wherein said kit further comprises an antioxidant, solvents and standards.

16. The in vitro method according to claim 14, wherein said kit further comprises a microfluidic chip and a coated surface for the immobilization of microvesicles/exosomes to a surface coated with molecules or agents having an affinity for said microvesicles/exosomes or being capable of binding microvesicular particles.

17. The in vitro method according to claim 16, wherein the molecules or agents having an affinity for said microvesicles or being capable of binding microvesicular particles are one or more of the group consisting of antibody species, proteins, aptamers, surfaces selectively restricting microvesicles from passage, and surfaces with selective adhesion to microvesicles.

18. The in vitro method according to claim 17, wherein said molecules or agents comprise proteins selected from the group consisting of lectin or sugar binding compounds.

19. The in vitro method according to claim 18, wherein said protein comprises lectin selected from the group consisting of

*Galanthus nivalis* lectin (GNA), *Narcissus pseudonarcissus* lectin (NPA), Concanavalin A, or cyanovirin.

20. The in vitro method according to claim 16, wherein the microfluidic chip comprises a coated surface as defined in claim 16.

21. The method according to claim 1, wherein said tumor sample is selected from the group consisting of tissue, cells, cell extracts, serum, whole blood, plasma concentrates, exosome factions, and precipitates from fractionation of plasma, blood, or body fluids.

22. The method according to claim 1, wherein the said tumor sample comprises exosomes.

23. The method according to claim 22 wherein said step of isolating said at least one phospholipid species comprises exposing said exosomes to a microfluidic chip.

* * * * *